(12) United States Patent
Högberg et al.

(10) Patent No.: US 7,708,889 B2
(45) Date of Patent: May 4, 2010

(54) BLOOD COMPONENT PROCESSING SYSTEM METHOD

(75) Inventors: Niclas Högberg, Karlskoga (SE); Emanuel Hällgren, Karlskoga (SE); Peter Pihlstedt, Stockholm (SE); Brian M. Holmes, Lakewood, CO (US); Lars Persson, Askersund (SE); Lars Strandberg, Gävle (SE); Geert Van Waeg, Brussels (BE); Frank Corbin, III, Littleton, CO (US)

(73) Assignee: CaridianBCT, Inc., Lakewood, CO (US)

( * ) Notice: Subject to any disclaimer, the term of this patent is extended or adjusted under 35 U.S.C. 154(b) by 0 days.

(21) Appl. No.: 12/359,738

(22) Filed: Jan. 26, 2009

(65) Prior Publication Data
US 2009/0127206 A1 May 21, 2009

Related U.S. Application Data

(62) Division of application No. 11/727,550, filed on Mar. 27, 2007, now Pat. No. 7,497,944, which is a division of application No. 10/414,475, filed on Apr. 16, 2003, now Pat. No. 7,279,107.

(60) Provisional application No. 60/373,083, filed on Apr. 16, 2002, provisional application No. 60/405,667, filed on Aug. 23, 2002.

(51) Int. Cl.
*B01D 37/04* (2006.01)
*B01D 61/00* (2006.01)
*B04B 11/04* (2006.01)

(52) U.S. Cl. ............ 210/650; 210/741; 210/745; 210/806; 210/97; 210/103; 210/143; 210/258; 210/295; 210/304; 210/360.1; 210/380.1; 210/416.1; 494/2; 494/36; 494/37; 494/45; 604/406; 604/408; 604/410

(58) Field of Classification Search ............ 210/650, 210/741, 745, 806, 97, 103, 143, 258, 295, 210/304, 360.1, 380.1, 416.1; 494/2, 36, 494/37, 45; 604/406, 408, 410
See application file for complete search history.

(56) References Cited

U.S. PATENT DOCUMENTS 1,684,870 A 9/1928 Lewis (Continued)

FOREIGN PATENT DOCUMENTS

DE 26 58 926 6/1978

(Continued)

OTHER PUBLICATIONS

"International Search Report", PCT/US03/11764, filed Apr. 16, 2003.

(Continued)

*Primary Examiner*—David A Reifsnyder
(74) *Attorney, Agent, or Firm*—Edna M. O'Connor; John R. Merkling; Laura B. Arciniegas

(57) ABSTRACT

A method used in connection with processing of blood components, wherein blood products are then filtered via a filter rotating along with a centrifuge rotor and the sensed pressure may be used in connection with controlling the pumping of the blood products and/or in connection with determining the location of an interface associated with the blood products.

55 Claims, 15 Drawing Sheets

U.S. PATENT DOCUMENTS

| | | |
|---|---|---|
| 2,616,619 A | 11/1952 | MacLeod |
| 2,878,995 A | 3/1959 | Dega |
| 3,096,283 A | 7/1963 | Hein |
| 3,145,713 A | 8/1964 | Latham, Jr. |
| 3,244,363 A | 4/1966 | Hein |
| 3,326,458 A | 6/1967 | Meryman et al. |
| 3,329,136 A | 7/1967 | Cadiou |
| 3,456,875 A | 7/1969 | Hein |
| 3,489,145 A | 1/1970 | Judson et al. |
| 3,519,201 A | 7/1970 | Eisel et al. |
| 3,600,900 A | 8/1971 | Buddecke |
| 3,679,128 A | 7/1972 | Unger et al. |
| 3,708,110 A | 1/1973 | Unger et al. |
| 3,724,747 A | 4/1973 | Unger et al. |
| 3,737,096 A | 6/1973 | Jones et al. |
| 3,771,715 A | 11/1973 | Baram |
| 3,823,869 A | 7/1974 | Loison |
| 3,825,175 A | 7/1974 | Sartory |
| 3,858,796 A | 1/1975 | Unger et al. |
| 3,864,089 A | 2/1975 | Tiffany et al. |
| 3,885,735 A | 5/1975 | Westbert |
| 3,987,961 A | 10/1976 | Sinn et al. |
| 4,007,871 A | 2/1977 | Jones et al. |
| 4,010,894 A | 3/1977 | Kellogg et al. |
| 4,016,828 A | 4/1977 | Maher, Jr. et al. |
| 4,059,967 A | 11/1977 | Rowe et al. |
| 4,091,989 A | 5/1978 | Schlutz |
| 4,094,461 A | 6/1978 | Kellogg et al. |
| 4,111,355 A | 9/1978 | Ishimaru |
| 4,131,369 A | 12/1978 | Gordon et al. |
| 4,132,349 A | 1/1979 | Khoja et al. |
| 4,142,670 A | 3/1979 | Ishimaru et al. |
| 4,146,172 A | 3/1979 | Cullis et al. |
| 4,187,979 A | 2/1980 | Cullis et al. |
| 4,198,972 A | 4/1980 | Herb |
| 4,230,263 A | 10/1980 | Westberg |
| 4,244,513 A | 1/1981 | Fayer et al. |
| 4,268,393 A | 5/1981 | Persidsky et al. |
| 4,269,718 A | 5/1981 | Persidsky |
| 4,278,202 A | 7/1981 | Westberg |
| 4,303,193 A | 12/1981 | Latham, Jr. |
| 4,304,357 A | 12/1981 | Schoendorfer |
| 4,322,298 A | 3/1982 | Persidsky |
| 4,350,283 A | 9/1982 | Leonian |
| 4,356,958 A | 11/1982 | Kolobow et al. |
| 4,386,730 A | 6/1983 | Mulzet |
| 4,387,848 A | 6/1983 | Kellogg et al. |
| 4,388,184 A | 6/1983 | Brous et al. |
| 4,389,206 A | 6/1983 | Bacehowski et al. |
| 4,389,207 A | 6/1983 | Bacehowski et al. |
| 4,405,079 A | 9/1983 | Schoendorfer |
| 4,413,771 A | 11/1983 | Rohde et al. |
| 4,413,772 A | 11/1983 | Rohde et al. |
| 4,416,654 A | 11/1983 | Schoendorfer et al. |
| 4,419,089 A | 12/1983 | Kolobow et al. |
| 4,421,503 A | 12/1983 | Latham, Jr. et al. |
| 4,425,112 A | 1/1984 | Ito |
| 4,430,072 A | 2/1984 | Kellogg et al. |
| 4,439,177 A | 3/1984 | Conway |
| 4,447,221 A | 5/1984 | Mulzet |
| 4,459,169 A | 7/1984 | Bacehowski et al. |
| 4,464,167 A | 8/1984 | Schoendorfer et al. |
| 4,482,342 A | 11/1984 | Lueptow et al. |
| 4,530,691 A | 7/1985 | Brown |
| 4,610,846 A | 9/1986 | Martin |
| 4,617,009 A | 10/1986 | Ohlin et al. |
| 4,647,279 A | 3/1987 | Mulzet et al. |
| 4,675,117 A | 6/1987 | Neumann et al. |
| 4,680,025 A | 7/1987 | Kruger et al. |
| 4,701,267 A | 10/1987 | Watanabe et al. |
| 4,708,710 A | 11/1987 | Dunn, Jr. |
| 4,708,712 A | 11/1987 | Mulzet |
| 4,720,284 A | 1/1988 | McCarty |
| 4,767,397 A | 8/1988 | Hohenberg et al. |
| 4,798,579 A | 1/1989 | Penhasi |
| 4,808,151 A | 2/1989 | Dunn, Jr. et al. |
| 4,834,890 A | 5/1989 | Brown et al. |
| 4,846,780 A | 7/1989 | Galloway et al. |
| 4,846,974 A | 7/1989 | Kelley et al. |
| 4,850,952 A | 7/1989 | Figdor et al. |
| 4,851,126 A | 7/1989 | Schoendorfer |
| 4,885,137 A | 12/1989 | Lork |
| 4,911,833 A | 3/1990 | Schoendorfer et al. |
| 4,915,847 A | 4/1990 | Dillon et al. |
| 4,925,442 A | 5/1990 | Bodelson |
| 4,933,291 A | 6/1990 | Daiss et al. |
| 4,934,995 A | 6/1990 | Cullis |
| 4,936,820 A | 6/1990 | Dennehey et al. |
| 4,936,998 A | 6/1990 | Nishimura et al. |
| 4,939,081 A | 7/1990 | Figdor et al. |
| 4,939,087 A | 7/1990 | Van Wie et al. |
| 4,940,543 A | 7/1990 | Brown et al. |
| 4,990,132 A | 2/1991 | Unger et al. |
| 5,006,103 A | 4/1991 | Bacehowski et al. |
| 5,032,288 A | 7/1991 | Columbus et al. |
| 5,076,911 A | 12/1991 | Brown et al. |
| 5,078,671 A | 1/1992 | Dennehey et al. |
| 5,089,146 A | 2/1992 | Carmen et al. |
| 5,100,564 A | 3/1992 | Pall et al. |
| 5,114,396 A | 5/1992 | Unger et al. |
| 5,160,310 A | 11/1992 | Yhland |
| 5,203,999 A | 4/1993 | Hugues |
| 5,213,970 A | 5/1993 | Lopez-Berestein et al. |
| 5,217,426 A | 6/1993 | Bacehowski et al. |
| 5,217,427 A | 6/1993 | Cullis |
| 5,224,921 A | 7/1993 | Dennehey et al. |
| 5,229,012 A | 7/1993 | Pall et al. |
| 5,282,982 A | 2/1994 | Wells |
| 5,298,171 A | 3/1994 | Biesel |
| 5,316,540 A | 5/1994 | McMannis et al. |
| 5,316,666 A | 5/1994 | Brown et al. |
| 5,316,667 A | 5/1994 | Brown et al. |
| 5,356,365 A | 10/1994 | Brierton |
| 5,360,542 A | 11/1994 | Williamson, IV et al. |
| 5,360,545 A | 11/1994 | Pall et al. |
| 5,362,291 A | 11/1994 | Williamson, IV |
| 5,370,802 A | 12/1994 | Brown |
| 5,397,497 A | 3/1995 | Jakobson et al. |
| 5,409,813 A | 4/1995 | Schwartz |
| 5,427,695 A | 6/1995 | Brown |
| 5,431,814 A | 7/1995 | Jorgensen |
| 5,437,624 A | 8/1995 | Langley |
| 5,472,621 A | 12/1995 | Matkovich et al. |
| 5,494,592 A | 2/1996 | Latham, Jr. et al. |
| 5,501,795 A | 3/1996 | Pall et al. |
| 5,529,691 A | 6/1996 | Brown |
| 5,543,062 A | 8/1996 | Nishimura |
| 5,547,591 A | 8/1996 | Hagihara et al. |
| 5,549,834 A | 8/1996 | Brown |
| 5,571,068 A | 11/1996 | Bacehowski et al. |
| 5,580,465 A | 12/1996 | Pall et al. |
| 5,587,070 A | 12/1996 | Pall et al. |
| 5,593,378 A | 1/1997 | Dyck |
| 5,607,830 A | 3/1997 | Biesel et al. |
| 5,628,915 A | 5/1997 | Brown et al. |
| 5,641,414 A | 6/1997 | Brown |
| 5,651,766 A | 7/1997 | Kingsley et al. |
| 5,656,163 A | 8/1997 | Brown |
| 5,674,173 A | 10/1997 | Hlavinka et al. |
| 5,690,815 A | 11/1997 | Krasnoff et al. |
| 5,690,835 A | 11/1997 | Brown |
| 5,702,357 A | 12/1997 | Bainbridge et al. |
| 5,704,887 A | 1/1998 | Slowik et al. |
| 5,704,888 A | 1/1998 | Hlavinka et al. |

| | | | |
|---|---|---|---|
| 5,704,889 A | 1/1998 | Hlavinka et al. | |
| 5,720,716 A | 2/1998 | Blakeslee et al. | |
| 5,722,926 A | 3/1998 | Hlavinka et al. | |
| 5,723,050 A | 3/1998 | Unger et al. | |
| 5,733,253 A | 3/1998 | Headley et al. | |
| 5,738,796 A | 4/1998 | Bormann et al. | |
| 5,759,147 A | 6/1998 | Bacehowski et al. | |
| 5,792,038 A | 8/1998 | Hlavinka | |
| 5,792,372 A | 8/1998 | Brown et al. | |
| 5,824,230 A | 10/1998 | Holm et al. | |
| 5,858,251 A | 1/1999 | Borchardt et al. | |
| 5,904,355 A | 5/1999 | Powers et al. | |
| 5,904,645 A | 5/1999 | Hlavinka | |
| 5,906,570 A | 5/1999 | Langley et al. | |
| 5,913,768 A | 6/1999 | Langley et al. | |
| 5,939,319 A | 8/1999 | Hlavinka et al. | |
| 5,951,877 A | 9/1999 | Langley et al. | |
| 5,954,626 A | 9/1999 | Hlavinka | |
| 5,976,388 A | 11/1999 | Carson | |
| 6,039,711 A | 3/2000 | Headley et al. | |
| 6,053,856 A | 4/2000 | Hlavinka | |
| 6,071,421 A | 6/2000 | Brown | |
| 6,071,422 A | 6/2000 | Hlavinka et al. | |
| 6,174,447 B1 | 1/2001 | Spindler | |
| 6,261,217 B1 | 7/2001 | Unger et al. | |
| 6,315,706 B1 | 11/2001 | Unger et al. | |
| 6,334,842 B1 | 1/2002 | Hlavinka et al. | |
| 6,348,031 B1 | 2/2002 | Unger et al. | |
| 6,354,986 B1 | 3/2002 | Hlavinka et al. | |
| 6,361,692 B1 | 3/2002 | Bischof | |
| 6,379,322 B1 | 4/2002 | Kingsley et al. | |
| 6,387,070 B1 | 5/2002 | Marino et al. | |
| 6,464,624 B2 | 10/2002 | Pages | |
| 6,605,223 B2 | 8/2003 | Jorgensen et al. | |
| 6,656,105 B2 | 12/2003 | Hogberg et al. | |
| 6,709,412 B2 | 3/2004 | Vandlik et al. | |
| 6,723,238 B2 | 4/2004 | Romanauskas et al. | |
| 7,029,430 B2 | 4/2006 | Hlavinka et al. | |
| 7,279,107 B2 | 10/2007 | Hogberg et al. | |
| 7,497,944 B2 * | 3/2009 | Hogberg et al. | 210/741 |
| 2001/0002743 A1 | 6/2001 | Jorgensen et al. | |
| 2002/0020680 A1 | 2/2002 | Jorgensen | |
| 2002/0091057 A1 | 7/2002 | Westberg et al. | |
| 2002/0123712 A1 * | 9/2002 | Gorsuch et al. | 210/650 |
| 2003/0173274 A1 | 9/2003 | Corbin et al. | |

FOREIGN PATENT DOCUMENTS

| | | |
|---|---|---|
| DE | 28 21 055 | 4/1979 |
| DE | 37 00 122 | 7/1988 |
| DE | 37 34 170 | 4/1989 |
| DE | 38 15 645 | 11/1989 |
| EP | 0 057 907 | 8/1982 |
| EP | 0 363 120 | 4/1990 |
| EP | 0 406 485 | 1/1991 |
| EP | 0 408 462 | 1/1991 |
| EP | 0 419 346 | 3/1991 |
| EP | 0 508 474 | 10/1992 |
| EP | 0 304 431 | 6/1993 |
| EP | 0 627 228 | 12/1994 |
| EP | 0 935 966 | 8/1999 |
| EP | 0 578 086 | 8/2001 |
| FR | 2 567 416 | 1/1986 |
| GB | 1 373 672 | 11/1974 |
| SE | 354 581 | 3/1973 |
| SE | 354 582 | 3/1973 |
| SU | 1091071 | 5/1984 |
| SU | 1236366 | 6/1986 |
| SU | 1255136 | 9/1986 |
| SU | 1725117 | 4/1992 |
| WO | WO 85/02561 | 6/1985 |
| WO | WO 87/06844 | 11/1987 |
| WO | WO 87/06857 | 11/1987 |
| WO | WO 89/02273 | 3/1989 |
| WO | WO 92/00145 | 1/1992 |
| WO | WO 94/02157 | 2/1994 |
| WO | WO 94/25086 | 11/1994 |
| WO | WO 94/27698 | 12/1994 |
| WO | WO 95/01842 | 1/1995 |
| WO | WO 95/04591 | 2/1995 |
| WO | WO 96/29081 | 9/1996 |
| WO | WO 96/32198 | 10/1996 |
| WO | WO 96/33023 | 10/1996 |
| WO | WO 96/40402 | 12/1996 |
| WO | WO 96/40403 | 12/1996 |
| WO | WO 97/15399 | 5/1997 |
| WO | WO 97/30715 | 8/1997 |
| WO | WO 97/30748 | 8/1997 |
| WO | WO 97/43045 | 11/1997 |
| WO | WO 98/35757 | 8/1998 |
| WO | WO 98/46362 | 10/1998 |
| WO | WO 98/50163 | 11/1998 |
| WO | WO 98/52629 | 11/1998 |
| WO | WO 00/54886 | 9/2000 |
| WO | WO 01/02037 A1 | 1/2001 |
| WO | WO 01/30364 A1 | 5/2001 |
| WO | WO 01/97943 A1 | 12/2001 |

OTHER PUBLICATIONS

"Extended European Search Report", EP 05020383.5, Feb. 7, 2006.
"Extended European Search Report", EP 08002589.3, Apr. 14, 2008.
Almici, et al, "Counterflow Centrifugal Elutriation:: Present and Future", *Bone Marrow Transplantation*, 1993, 12:105-108.
Angelbeck, Judy, *Adverse Reactions to Platelet Transfusion, Risks and Probable Causes*, 1994, pp. 1-14.
Baxter: "Fenwal CS-3000, Plus Blood Cell Separator Operator's Manual", 1987.
Baxter: Baxter CS-3000 Plus Blood Cell Separator, Technology with a Mind you a ca.
Baxter: Fenwal: CS-300 0 Blood Cell Separator, Powerful Technology, Fenwal Laboratories, undated.
Beckman: "Centrifugal Elutriation: How It Works . . . ", product brochure for Beckman centrifuges, pp. 1-7, vi., undated.
Besso et al, "Asahi Sepacell* R-500 Leukocyte Removal Filter: The Effects of Saline Flush on the Unloading of White Blood Cells and contamination of the Filtrate", Pall Technical Report, Pall Biomedical Products Corporation, East Hills, New York, 1991.
Besso, et al, "Asahi Sepacell PL-10A Leukocyte Removal Filter: Effect of Post-Filtration Flush with saline", Pall Technical Report, 1991.
Biofil. Systems Filtration of Haemocomponents, undated.
Brandwein et al, "Asahi Sepacell PL-10A Leukocyte Removal Filter Description and Review of Claims", Pall Technical Report, 1991.
Brandwein et al, "Asahi Sepacell PL10A leukocyte Removal Filter: efficiency with Random Donor Platelet Pools,", Pall Technical Report, undated.
Brown et al, "Evaluation of a new Separation Method Utilizing Plasma Recirculation and Autoelutrition", *Transfusion*, 1994, v. 34, Supp.
Bruil et al, "Asymmetric membrane filters for the removal of leukocytes from blood", *J. Biomedical Materials Research*, vol. 25, 1459-1480, 1991.
Buchanan et al, "Principle of a Counter-streaming Centrifuge for the Separation of Particles of Different Sizes", *Nature* May 24, 1948, pp. 648-649 [Lindahl].
Burgstaler et al, "White Blood Cell Contamination of Apheresis Platelets Collected on the COBE Spectra", COBE Blood Component Technology.
COBE Spectra Apheresis System, *Operator's Manual*, (software rev. 3.0-3.9), Feb. 1991, pp. 8-1 and 8-3-8-34.
COBE: Price et al, "Platelet Collection using the COBE Spectra", COBE Blood Component Technology, 1981.
Contreras et al, "A Comparison of Methods to Wash Liquid-Stored Red Blood Cells and Red Blood Cells Frozen with High or Low Concentrations of Glycerol", *Transfusion*, Nov.-Dec. 1976, 539-565.

Dijkstra: "Multi-Chamber Centrifugation System", Dijkstra Vereenigde BV, 13 pages, undated.

Drumheller et al, "The Effects of RPM and Recycle on Separation Efficiency in a Clinical Blood Cell Centrifuge", *J. of Biomechanical Engineering*, Nov. 1987, v. 109, pp. 324-329.

Dzik, Sunny, Leukodepletion Blood Filters: Filter Design and Mechanisms of Leukocyte Removal, *Transfusion Medicine Review*, v. VII, No. 2, May 1993, pp. 65-77.

Faradji et al, "Large Scale Isolation of Human Blood Monocytes by Continuous Flow Centrifugation Leukapheresis and Counterflow Centrifugation Elutriation for Adoptive Cellular Immunotherapy in Cancer Patients", *J. Immunological Methods*, 174:297-309, 1994.

Figdor et al, "Isolation of Functionally Different Human Monocytes by Counterflow Centrifugation Elutriation", *Blood*, v 60, No. 1, pp. 46-52, undated.

Figdor et al, "Theory and Practice of Centrifugal Elutriation (CE), Factors Influencing the Separation of Human Blood Cells", *Cell Biophysics 5*, 105-118, 1983.

Freedman, et al, "White Cell Depletion of Red Cell and Pooled Random-Donor Platelet Concentrates by Filtration and Residual Lymphocyte Subset Analysis", *Transfusion*, 1991, v 31, No. 5, pp. 433-440.

*Fresenius MT AS 104 Blood Cell Separator, Operating Instructions*, Fresenius Apr. 6, 1990 (OP). by separate chapter.

Fresenius: "Operating Instructions AS 104 Blood Cell Separator", May 7, 1990, p. 01-06; 1-3 to 1-6; 1-23. Edit.

Gao et al, "Implementation of a Semi-closed Large Scale Centrifugal Elutriation System", *J. Clinical Apheresis*, 3:154-160, 1987.

Grabske, Robert, "Separating Cell Populations by Elutriation", Beckman Instruments, 1978, p. 1-8.

Griffith, Owen, "Separation of T and B Cells from Human Peripheral Blood by Centrifugal Elutriation", *Analytical Biochemistry*, 1978, 87:97-107.

*Haemonetics Mobile Collection System Owner's Operating and Maintenance Manual*, 1991, pp. 1-6 and pp. 3-2 through 3-7.

Haemonetics: "Haemonetics Leukocyte Management System", [1992].

Haemonetics: "Haemonetics MCS +LN 9000 Platelet Protocols".

Haemonetics: "The Mobile Collection System Gives you Easier Access to More Donors than Ever Before", Haemonetics, Sep. 1992.

Heddle et al, "A Prospective Study to Identify the Risk Factors Associated with Acute Reactions to Platelet and Red Cell Transfusion", *Transfusion*, 1993, 33:794-797.

Heddle et al, The Role of the Plasma from Platelet Concentrates in Transfusion reactions, *New England Journal of Medicine*, Sep. 8, 1994, 331(10):625-628, 670-71.

Högman,Claes, ed., *Leucocyte Depletion of Blood Components*, 1994, pp. 1, 156-173.

Jemionek et al, "Variations in CCE Protocol for Cell Isolation", *Elutriation*, pp. 17-41, undated.

Kauffman et al, "Isolation of Cell Cycle Fractions by Counterflow Centrifugal Elutriation", *nalytical Biochemistry*, 1990, 191:41-46.

Keng et al, "Characterization of the Separation Properties of the Beckman Elutriator System", *Cell Biophysics*, 1981, 3:41-56.

Lindahl, P.E., "On Counter Streaming centrifugation in the Separation of Cells and Cell Fragment", *Biochemica et Biophysica Acta*, v. 21, 1956, pp. 411-415.

Oxford et al, Interface Dynamics in a Centrifugal Cell Separator, *Transfusion*, Nov.-Dec. 1988, 28(6):588-592.

Oxford, et al, Monitoring and Automated Optimization of a Cell Centrifuge ,IEEE Eighth Annual Conference of the Engineering in Medicine and Biology Society, p. 925-927, (undated).

Pall: "Lower is Better", Pall Biomedical Products Company, East Hills, New York, 1994.

Pall: "LRF6/LRF10, High Efficiency Leukocyte Removal Filter Systems for Platelets", Pall Biomedical Products Corporation, East Hills, New York, undated.

Pall: "Transfusion Associated CMV: Benefits of Leukocyte Filtration for Red Cell and Platelet Blood Products: Questions and Answers", 1994, pp. 1-19. Edit.

Persidsky et al, "Separation of Platelet-rich Plasma by Modified Centrifugal Elutriation", *J. of Clinical Apheresis*, 1982, 1:18-24.

Plas et al, "A New Multi-Chamber Counterflow Centrifugation Rotor with High-separation Capacity and Versatile Potentials", *Experimental Hemotology*, 1998, 16:355-359.

Runck et al, "Continuous-flow Centrifugation Washing of Red Blood Cells", *Transfusion*, Jul.-Aug. 1972, pp. 237-244.

Sakalas et al, "Evaluation of Two New High Performance Leucocyte Removal Filters (ASAHI PLS-5A PLS-10A) for Use with Platelet Components", Hogman, ed., *Leucocyte Depletion of Blood Components*, VU University Press, Amsterdam, 1994, pp. 161-165.

Sanderson, Richard J., "Separation of Different Kinds of Nucleated Cells from Blood by Centrifugal Elutriation", *Cell Separation Methods and Selected Applications*, 1982, 1:153-168.

Seghatchian et al, "Leucocyte Depletion by Filtration is Associated with Changes in Platelet Aggregation states: A New Diagnostic Approach", Hogman, ed., *Leucocyte Depletion of Blood Components*, VU University Press, Amsterdam, 1994, pp. 171-173.

Seghatchian et al, "Leucocyte Depletion of Platelet Concentrates: Is Poor Filtration Recovery Related to Activation/Aggregation States of Platelets?", Hogman, ed., *Leucocyte Depletion of Blood Components*, VU University Press, Amsterdam, 1994, pp. 167-170.

Sniecinski, I., "Prevention of Immunologic and Infectious Complications of Transfusion by Leukocyte Depletion, " *Clinical Application of Leukocyte Depletion*, ed., Sekiguchi, S., Blackwell Science Inc, Great Britain, Aug. 1993, pp. 202-211.

Stack et al, Cytokine Generation in Stored Platelet Concentrates, *Transfusion*, 1994, 34:20-25.

Takahashi et al, "Bradykinin Formation in a Platelet Concentrate Filtered with a Leukocyte-removal Filter made of Nonwoven Polyester Fibers with a Negatively Charged Surface", undated.

Tulp et al, "A Separation Chamber to Sort Cells and Cell Organelles by Weak Physical Forces . . . ", *J. of Immunological Methods*, 1984, 69:281-295.

Van Wie et al, "The Effect of Hematocrit and Recycle on Cell Separations", *Plasma Ther Transfus Technal* 1986; 7:373-388.

Van Wie, Bernard, "Conceptualization and Evaluation of Techniques for Centrifugal Sepration of Blood Cells: Optimum Process Conditions, Recycle and Stagewise Processing", Dissertation, 1982, *UMI Dissertation Services*, Ann Arbor, Michigan, pp. 27-58.

Whitbread et al, "Performance Evaluation of the Sepacell PL-10A Filter and Pall PXL8 filter: Measurement of Leukocyte Residuals and Consistency"; Pall Technical Report, Pall Biomedical Corporation, 1991, East Hills, New York., undated.

Whitbread et al, "Reduction of C3A Fragment Levels following Leukodepletion using a Pall PX18 Filter", undated.

* cited by examiner

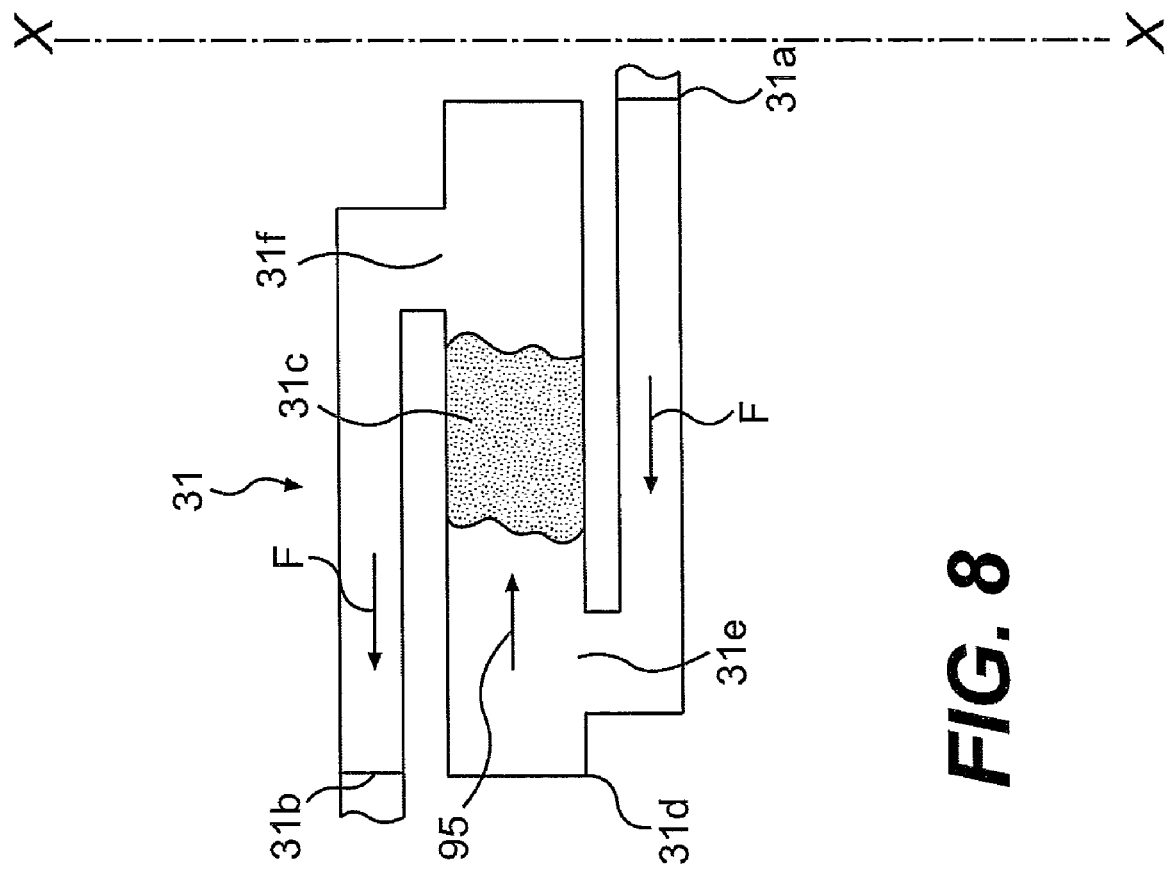
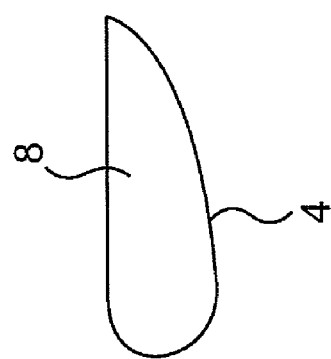
FIG. 8

BLOOD COMPONENT PROCESSING SYSTEM METHOD

This application is a division of U.S. application Ser. No. 11/727,550 filed on Mar. 27, 2007, now U.S. Pat. No. 7,497,944 B2, which is a division of U.S. application Ser. No. 10/414,475 filed on Apr. 16, 2003, now U.S. Pat. No. 7,279,107, which claims the benefit of U.S. provisional patent application No. 60/373,083, filed Apr. 16, 2002, and No. 60/405,667, filed Aug. 23, 2002.

BACKGROUND OF THE INVENTION

1. Field of the Invention

The present invention relates to a system, apparatus, and method for processing components of blood. In particular, some aspects of the invention relate to processing blood components through the use of centrifugal separation, filtration, and/or any other form of processing.

2. Description of the Related Art

Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In terms of size, the particle constituents are related, in order of decreasing size, as follows: white blood cells, red blood cells, and platelets. Most current separation devices rely on density and size differences or surface chemistry characteristics to separate blood components.

Separation of certain blood components is often required for certain therapeutic treatments involving infusion of particular blood components into a patient. For example, in a number of treatments involving infusion of platelets, there is sometimes a desire to separate out at least some leukocytes and/or red blood cells before infusing a platelet-rich blood component collection into a patient.

For these and other reasons, there is a need to adopt approaches to processing components of blood.

SUMMARY

In the following description, certain aspects and embodiments of the present invention will become evident. It should be understood that the invention, in its broadest sense, could be practiced without having one or more features of these aspects and embodiments. It should also be understood that these aspects and embodiments are merely exemplary.

One aspect of the invention relates to a system for processing blood components. The system may comprise a separation chamber including a chamber interior in which blood components are centrifugally separated and an outlet port for passing at least some centrifugally separated blood components from the chamber interior. A flow path may be in flow communication with the outlet port of the separation chamber. The apparatus may further comprise a filter including a filter inlet in flow communication with the flow path, a porous filtration medium configured to filter at least some of at least one blood component (e.g., leukocytes, platelets, and/or red blood cells) from centrifugally separated blood components passed to the filter via the flow path, and a filter outlet for filtered blood components. The system may further comprise a rotor configured to be rotated about an axis of rotation. The rotor may comprise a first portion configured to receive the separation chamber and a second portion configured to receive the filter, wherein the first and second portions may be positioned with respect to one another so that when the separation chamber is received in the first portion and the filter is received in the second portion, the filter is closer than the interior of the separation chamber to the axis of rotation. The system may be configured so that the rotor rotates during filtering of at least one blood component via the filter.

In another aspect, the system may be configured so that when the filter is received in the second portion, the filter is eccentric with respect to the axis of rotation. For example, the system may be configured so that the filter is at least close to the axis of rotation (i.e., close to the axis of rotation or intersecting the axis of rotation at least partially) and so that the axis of rotation does not intersect an interior flow path defined by the filter. In some examples, when the filter is received in the second portion, the filter may be offset from the axis of rotation so that the axis of rotation does not intersect the filter. In some examples, the filter is eccentrically positioned so that blood components exit a housing of the filter (and/or enter the filter itself) at a location that is at least close to the rotor's axis of rotation, as compared to the location where the blood components enter the filter housing (and/or where the blood components exit the filter itself).

In a further aspect, the system may be configured so that when the filter is received in the second portion, a filter housing outflow port is located closer than a filter housing inflow port and/or the porous filtration medium to the axis of rotation. In another aspect, the filter housing outflow port may be above the filter housing inflow port.

In an additional aspect, the filter may comprise a filter housing defining an interior space containing the porous filtration medium, wherein the filter inlet and filter outlet may be in flow communication with the interior space, and wherein the system may be configured so that when the filter is received in the second portion, the filter is positioned so that blood components flow in the interior space in a direction facing generally toward the axis of rotation. In some examples, the filter housing defines a filter housing inflow port for passing blood components to the interior space and a filter housing outflow port for passing blood components from the interior space. The system may be configured so that when the filter is received in the second portion, the filter housing outflow port is closer than the filter housing inflow port (and/or the porous filtration medium) to the axis of rotation. In an exemplary arrangement, the filter housing outflow port is above the filter housing inflow port.

In a further aspect, the second portion may comprise at least one of a ledge and a slot configured to receive the filter, the at least one of a ledge and a slot being positioned under a top surface of the rotor. Alternatively (or additionally), the rotor may comprise a holder configured to hold the filter with respect to the rotor.

There are many possible arrangements for the flow path. In some examples, the flow path may include tubing. For example, the flow path may include a first tubing portion having one end coupled to the outlet port of the separation chamber and another end coupled to the filter inlet. In addition, the apparatus may also include a second tubing portion having an end coupled to the filter outlet, wherein the second tubing portion extends in a direction facing generally away from the axis of rotation. Further, the system may include a third tubing portion downstream from the second tubing portion, wherein the third tubing portion extends in a direction facing generally toward the axis of rotation.

In one more aspect, the rotor may comprise a groove configured to receive at least some of the tubing (e.g., at least some of the second and third tubing portions).

One other aspect relates to an apparatus for use with a centrifuge for processing blood components. The apparatus could be configured in a number of different ways. According to one aspect, the apparatus may comprise the separation chamber, the flow path, and the filter. In some embodiments, the apparatus is configured to be disposed after being used for processing of blood components.

In some embodiments, the rotor's axis of rotation may extend through the second portion of the rotor.

In another aspect, the system may comprise at least one valving member on the centrifuge rotor, the valving member being configured to control flow of at least some of the blood components during rotation of the rotor. In some examples, the valving member may comprise a tubing clamp.

In a further aspect, the system may comprise at least one sealing member on the centrifuge rotor, the sealing member being configured to create a seal during rotation of the rotor. For example, the sealing member may comprise a tubing welder.

In one further aspect, the rotor may comprise at least one support member configured to support the chamber, wherein the at least one support member may comprise a guide groove configured to receive a portion of the tubing line and a controllable clamp and/or welder associated with the groove. For example, the clamp may be configured to controllably occlude flow of blood components through the tubing line. In some examples, the chamber may comprise at least one guide hole configured to receive the at least one support member.

In some embodiments, the rotor may comprise a plurality of support members located in an asymmetric fashion with respect to the axis of rotation, and the chamber may comprise a plurality of guide holes, each of the guide holes being configured to receive a respective one of the support members.

According to another aspect, the system may further comprise a pump configured to pump at least some blood components from the chamber. The system may also comprise a pressure sensor configured to sense pressure of the pumped blood components, wherein the system may be configured to control the pump based on at least the pressure sensed by the pressure sensor.

A further aspect relates to a system comprising a chamber (e.g., a blood separation chamber) that may comprise an interior configured to contain separated blood components, and an outlet port for passing at least some of the separated blood components from the interior. A flow path may be in flow communication with the outlet port of the chamber. The system may further comprise a filter comprising a filter inlet in flow communication with the flow path, a porous filtration medium configured to filter at least some of at least one blood component from separated blood components passed to the filter via the flow path, and a filter outlet for filtered blood components. In addition, the system may also comprise a pump configured to pump at least some of the separated blood components from the chamber to the filter via the flow path, and a pressure sensor configured to sense pressure of blood components pumped to the filter. The system may be configured to control the pump based on at least the pressure sensed by the pressure sensor.

In some embodiments, the pump may comprise a portion of a centrifuge and/or at least a portion of a blood component expresser.

According to another aspect, the system may be configured such that the system calculates a difference between pressures sensed by the pressure sensor in at least one time interval, determines when the calculated difference is at least a predetermined amount, and controls the pump in response to at least the determination that the calculated difference is at least the predetermined amount.

In yet another aspect, there is a system that may comprises a separation chamber comprising a chamber interior in which blood components are centrifugally separated, and an outlet port for passing at least some of the centrifugally separated blood components from the chamber interior. A flow path may be in flow communication with the outlet port of the separation chamber. The system also may comprise a pump configured to pump at least some of the centrifugally separated blood components from the chamber and through the flow path, and a pressure sensor configured to sense pressure of blood components pumped by the pump. In addition, the system may comprise a centrifuge rotor configured to be rotated about an axis of rotation, the rotor comprising a portion configured to receive the separation chamber. The system may be configured such that the system calculates a difference between pressures sensed by the pressure sensor in at least one time interval, determines when the calculated difference is at least a predetermined amount, and controls the pump in response to at least the determination that the calculated difference is at least the predetermined amount.

Many different types of chambers are possible. In some embodiments, the chamber may have a ring shape.

According to another aspect, the chamber may comprise a bag (e.g., a blood component separation bag). For example, at least a portion of the bag may be formed of at least one of flexible and semi-rigid material so that the chamber interior has a variable volume. In some embodiments, the bag may have a generally annular ring shape defining a central opening.

In another aspect, the chamber interior may include a tapered portion leading to the outlet port.

In a further aspect, the chamber may be configured so that the chamber has a variable volume, and the pump may be configured to reduce the volume of the chamber interior. In one example, the pump may be configured to apply pressure to the chamber via hydraulic fluid. Such an example may also include a sensor configured to sense pressure of pumped blood products, wherein the sensor may be configured to sense pressure of the hydraulic fluid. Certain aspects of the invention could be practiced with or without a pump and/or pressure sensor, and when such structure is present, there are many possible forms of pumping and sensing configurations that could be used.

In an even further aspect, the system may further comprise an optical sensor, and the system may be configured to control the pump based on at least one of information sensed by the optical sensor and pressure sensed by the pressure sensor. In one example, an optical sensor may be positioned to sense blood components in the chamber, and/or an optical sensor may be positioned to sense blood components at another location, such as a location associated with the flow path (e.g., at a tubing line in flow communication with the filter).

In another aspect, the system may be configured so that the pump pumps blood components from the chamber during rotation of the centrifuge rotor.

In a further aspect, the apparatus may further comprise a collection container comprising an inlet in flow communication with the filter outlet and/or the flow path, and/or a portion of the rotor may further comprise a cavity configured to receive the collection container and possibly also the filter. In some examples, there may be more than one collection container and/or at least one collection container may be located outside of a centrifugal field during blood component processing.

One more aspect of the invention relates to a method of processing blood components.

Some exemplary methods may include providing a system disclosed herein. The term "providing" is used in a broad sense, and refers to, but is not limited to, making available for use, manufacturing, enabling usage, giving, supplying, obtaining, getting a hold of, acquiring, purchasing, selling, distributing, possessing, making ready for use, forming and/or obtaining intermediate product(s), and/or placing in a position ready for use.

In one more aspect, a method may comprise placing a separation chamber in a first portion of a centrifuge rotor and a filter in a second portion of the rotor, wherein the filter is located closer than an interior of the separation chamber to the axis of rotation of the rotor, and wherein the filter comprises a porous filtration medium. The method may further comprise rotating the centrifuge rotor, the separation chamber, and the filter about the axis of rotation of the centrifuge rotor, wherein the blood components are centrifugally separated in the chamber interior. In addition, the method may comprise removing at least some of the centrifugally separated blood components from the separation chamber, and filtering the removed blood components with the filter so as to filter at least some of at least one blood component (e.g., leukocytes, platelets, and/or red blood cells) from the removed blood components, wherein at least a portion of the filtering occurs during said rotating.

In another aspect, the method may further comprise pumping at least some of the centrifugally separated blood components from the chamber to the filter. A further aspect may include sensing pressure of pumped blood components, and controlling the pumping based on at least the sensed pressure.

In yet another aspect, there is a method comprising pumping at least some separated blood components from a chamber (e.g., a blood separation chamber or any other type of chamber structure), filtering the pumped blood components with a filter so as to filter at least some of at least one blood component from the pumped blood components, sensing pressure of blood components pumped to the filter, and controlling the pumping based on at least the pressure sensed by the pressure sensor. In some examples, the chamber may be rotated (e.g., via a centrifuge) and separated blood components may be pumped from the chamber while the chamber is received on a centrifuge rotor and/or after the chamber is removed from a centrifuge rotor.

A further aspect relates to a method of determining a location of at least one interface during processing of blood components, wherein the method comprises pumping at least some centrifugally separated blood components from a chamber, sensing pressure of the pumped blood components, and determining a location of at least one interface based on the sensed pressure, wherein the interface is associated with the pumped blood components. For example, the interface may be an interface between blood components and air, and/or an interface between differing blood components.

In another aspect, the method may comprise calculating a difference between pressures sensed in at least one time interval, determining when the calculated difference is at least a predetermined amount, and controlling the pumping in response to at least the determination that the calculated difference is at least the predetermined amount.

According to another aspect, there is a method of processing blood components, comprising rotating a chamber about an axis of rotation, wherein blood components are centrifugally separated in the chamber, pumping at least some separated blood components from the chamber, sensing pressure of pumped blood components, calculating a difference between pressures sensed in at least one time interval, determining when the calculated difference is at least a predetermined amount, and controlling the pumping in response to at least the determination that the calculated difference is at least the predetermined amount.

In another aspect, the method may further comprise passing blood components (e.g., filtered blood components) into at least one collection bag.

In a further aspect, the blood components in the chamber may be blood components of a buffy coat. Buffy coat blood components are generally blood components that result from a procedure where platelets and leukocytes along with some amount of red blood cells and plasma have been separated from whole blood. Alternatively, any other substance containing one or more blood components could be processed.

In some examples, whole blood may be processed in the method. For example, whole blood may be introduced into the chamber (e.g., from one/or more donors, and/or from one or more containers containing blood donated by one or more donors). In the processing of whole blood, any number of blood components may be centrifugally separated, filtered, and/or processed in any other way. For example, components of whole blood may be separated and pumped into separate, respective containers (optionally while being filtered via one or more filters).

In one more aspect, when blood components are pumped, the pumping may comprise reducing the volume of an interior of the chamber. For example, the method may comprise applying pressure to the chamber via hydraulic fluid.

In another aspect, the pumping may occur during rotation of a centrifuge rotor.

In yet another aspect, the method may comprise optically sensing pumped blood products, and controlling the pumping based on at least one of optically sensed information and sensed pressure. For example, the optically sensing may comprise optically sensing blood components in the chamber and/or optically sensing blood components in a tubing line (e.g., a tubing line in flow communication with a filter).

In another aspect, the method may further comprise causing at least one valving member on the centrifuge rotor to control flow of at least some of the blood components during rotation of the rotor. As mentioned above, the valving member may comprise a tubing clamp.

In a further aspect, the method may further comprise causing at least one sealing member on the centrifuge rotor to create a seal during rotation of the rotor. As mentioned above, the sealing member may comprise a tubing welder.

Aside from the structural and procedural arrangements set forth above, the invention could include a number of other arrangements such as those explained hereinafter. It is to be understood that both the foregoing description and the following description are exemplary only.

BRIEF DESCRIPTION OF THE DRAWINGS

The accompanying drawings are incorporated in and constitute a part of this specification. The drawings illustrate exemplary embodiments and, together with the description, serve to explain some principles of the invention. In the drawings.

FIG. 8 is a schematic, partial cross-section view illustrating the configuration of a filter and separation chamber associated with the system embodiment of FIG. 1B;

DESCRIPTION OF A FEW EXEMPLARY EMBODIMENTS

Figure 1:
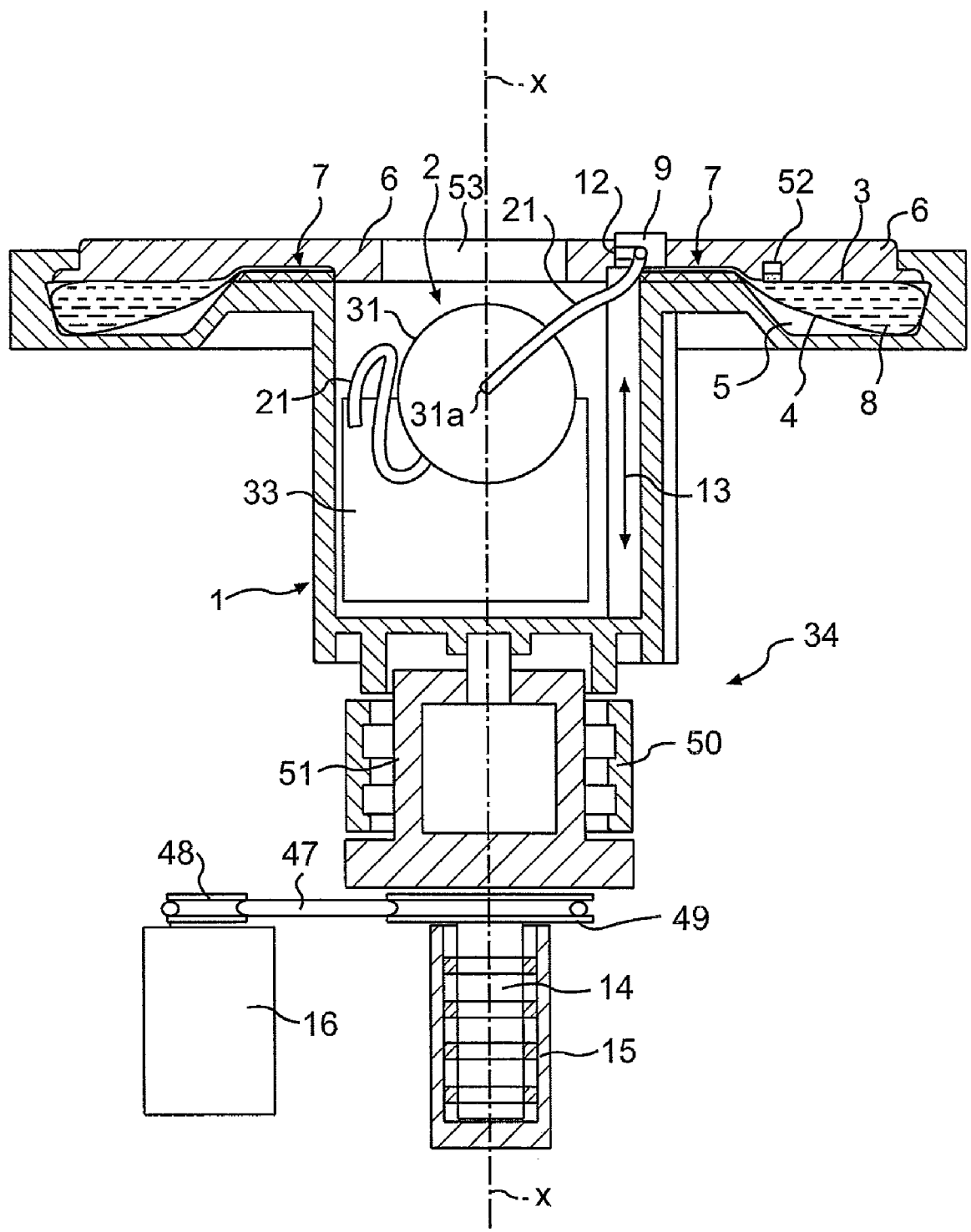
FIG. 1 is a schematic cross-section view of an embodiment of a system in accordance with the present invention.

Reference will now be made in detail to a few exemplary embodiments of the invention. Wherever possible, the same reference numbers are used in the drawings and the description to refer to the same or like parts.

FIG. 1 shows an embodiment of a system for processing blood components. The system includes a centrifuge 34 in combination with an apparatus including a filter 31 and a chamber 4 in the form of a blood component separation bag having a ring shape. The centrifuge 34 has a rotor 1 including a first rotor portion defining a ring-shaped area 3 receiving the chamber 4 and a second rotor portion defining a center cavity 2 where the filter 31 and possibly also a collection container 33 (e.g., a bag used to contain blood components processed by the system) may be located during a blood component processing operation.

The chamber 4 has an interior 8 in which blood components are centrifugally separated during rotation of the rotor 34 about an axis of rotation X. As described in more detail below, at least some of the blood components centrifugally separated in the chamber 4 are passed via a tubing line 21 to a filter 31 where at least some of at least one blood component (e.g., leukocytes, platelets, and/or red blood cells) is filtered before passing the filtered blood component(s) to the collection container 33.

As described in more detail below, hydraulic fluid in a space 5 located beneath the chamber 4 exposes the chamber 4 to an external pressure that causes at least some centrifugally separated blood components to be pumped from the chamber 4. The centrifuge rotor 1 also has an inner lid 6 adapted to rotate along with a remainder of the rotor 1 and the separation chamber 4. The lid 6 is optionally configured to at least partially secure the chamber 4, for example, in a clamping fashion along a line 7 shown in FIG. 2. This may be an effective way to fix the position of the chamber 4 in the centrifuge rotor 1 and limit the stresses on the inner edge of the bag 1. The centrifuge lid 6 optionally defines a central opening 53 possibly allowing center cavity 2 to be accessible externally even when the inner lid 6 is in a closed position.

Figure 1A:
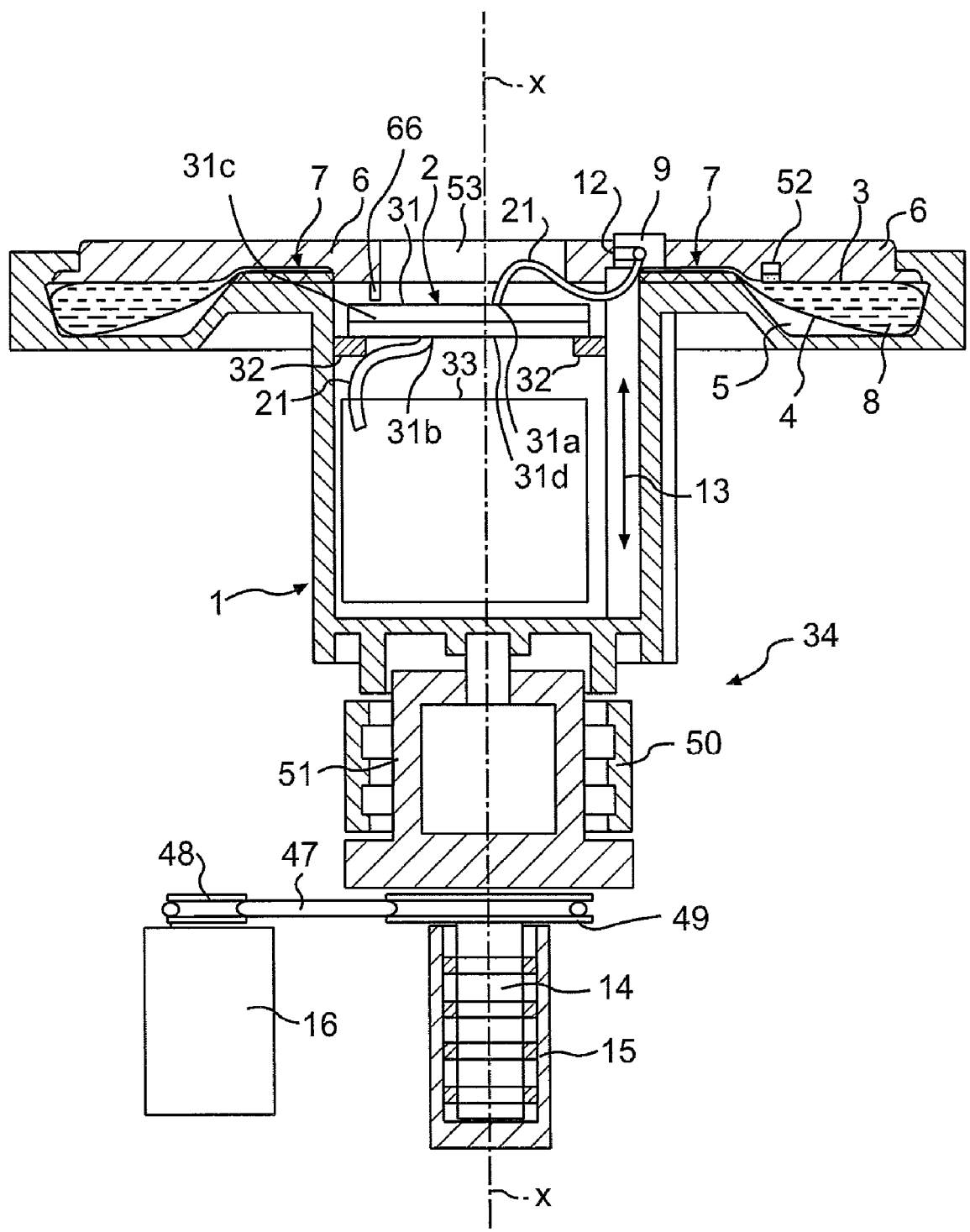
FIG. 1A is a view similar to that of FIG. 1 showing an alternate embodiment of the system.
Figure 1B:
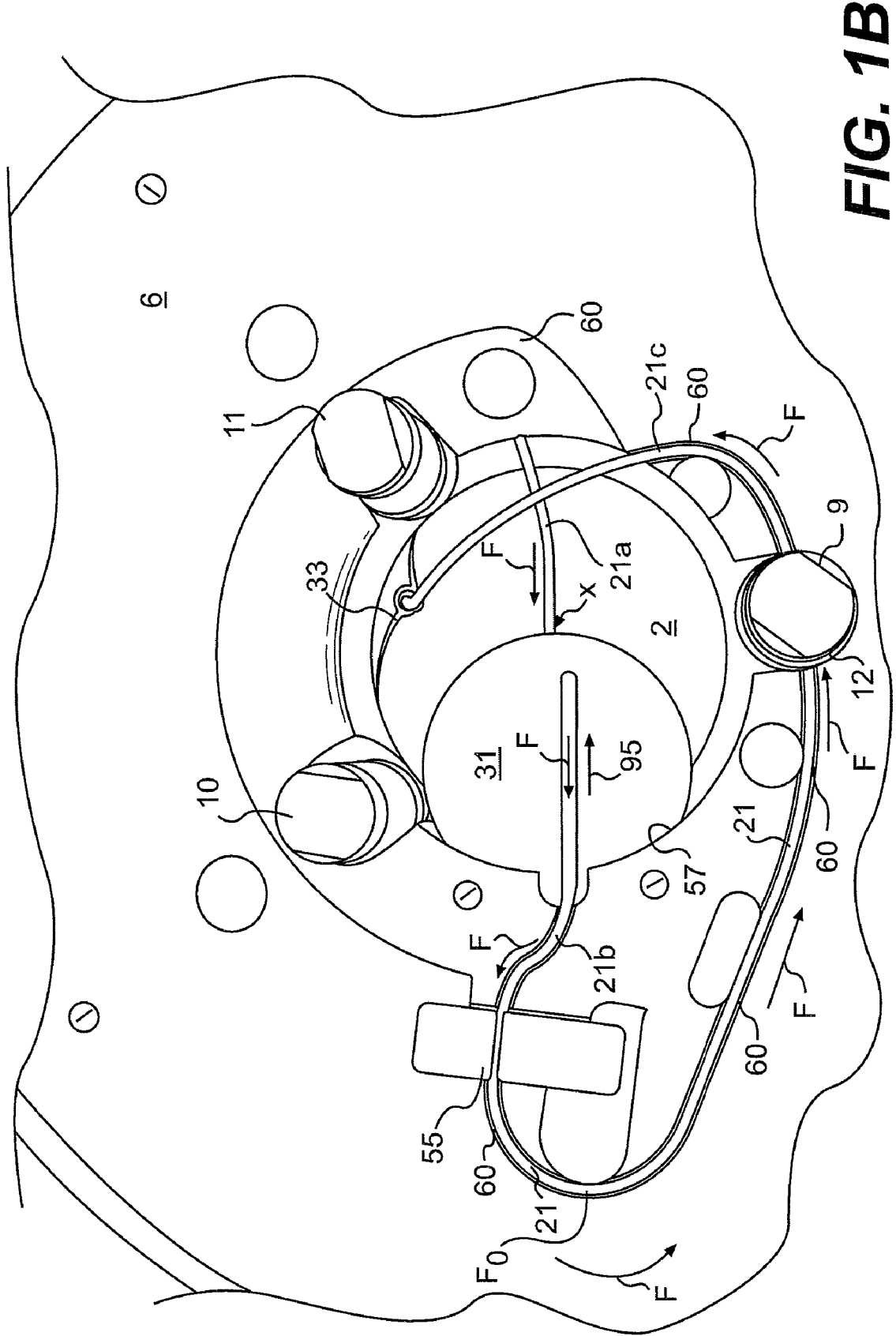
FIG. 1B is a top plan view of another alternative embodiment of the system.
Figure 2:
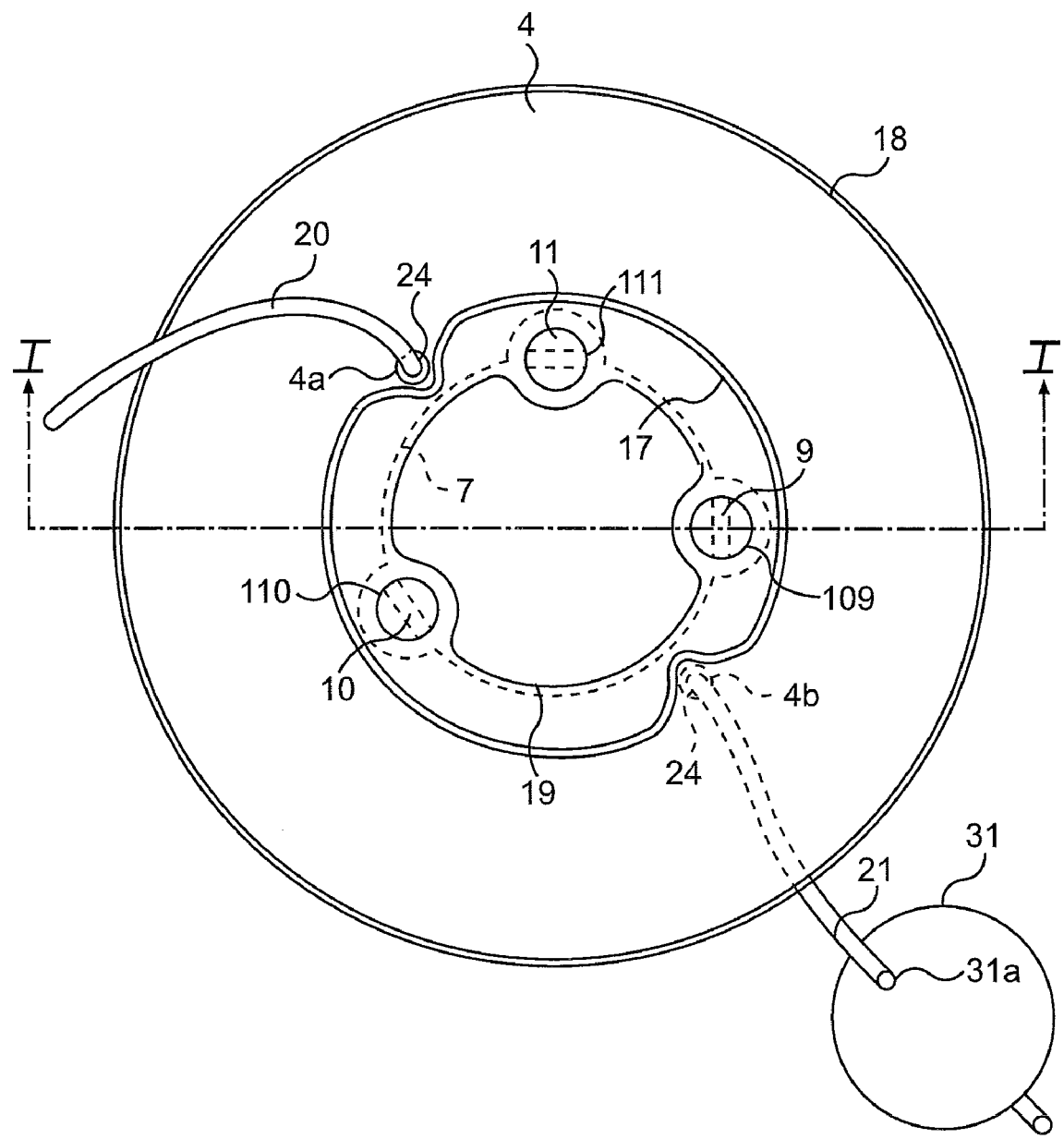
FIG. 2 is a top plan view of a portion of an apparatus including a chamber and filter for use with the systems of FIGS. 1, 1A, and 1B, wherein line I-I of FIG. 2 represents the plane for the cross-section views of the chamber portion shown in FIGS. 1 and 1A.
Figure 4:
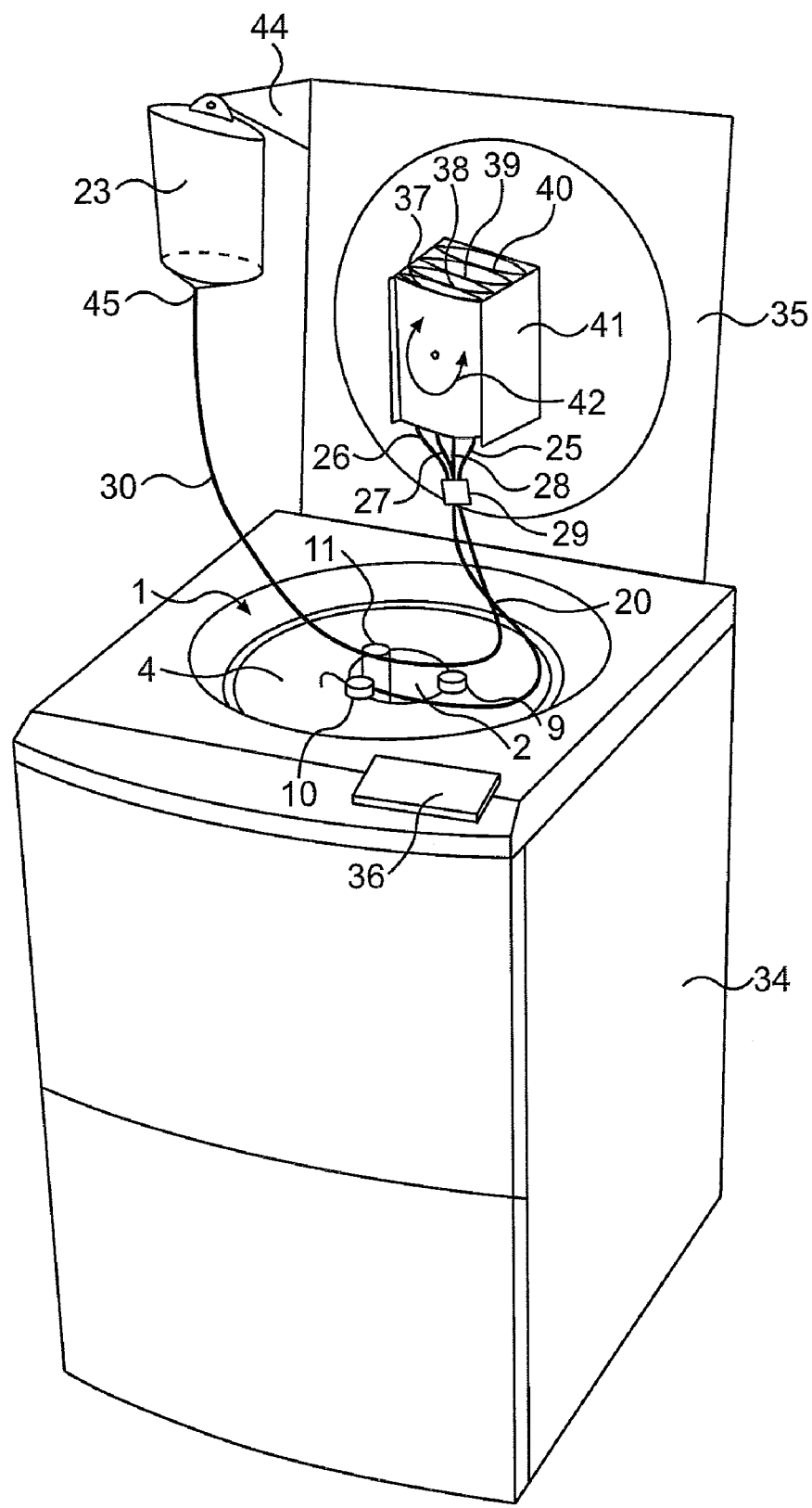
FIG. 4 is an isometric view of a system including the apparatus of FIG. 3.

The centrifuge rotor 1 may include one or more supports 9, 10, 11 shown in FIGS. 1B, 2, and 4 (for example, three to five supports). (The view of FIG. 1 shows only support 9.) Optionally, the supports extend wholly or partially in the center cavity 2 and thus may define the cavity 2. The above-mentioned clamping of the chamber 4 by the inner lid 6 may limit, through its greater contact area, the load on the inner edge of the chamber 4 and assist in preventing it from slipping over or being released in some other way from supports 8, 9, and 10 during centrifuge rotor rotation. As shown in FIGS. 1B and 2, e.g., the respective supports 9-11 are optionally somewhat asymmetric (e.g., about the rotational axis X), and may thus assist in defining the position of the chamber 4 and its associated tubes in the rotor 1 while holding the chamber 4 in position during centrifuging.

Each of the support members 9-11 may define a respective guide groove, such as groove 12 shown in FIG. 1, which is defined in support 9. The groove may be shaped to receive one or more different tubes passing blood components or other fluids in the system. One or more of the supports 9-11 may be configured so that the guide grooves may be selectively reduced (and/or increased) in size to clamp (and/or unclamp) tubing placed in the grooves, and thereby accomplish valving for regulating the flow of fluids in the apparatus. For example, a portion of the support 9 could be configured to move in a clamping/unclamping fashion in the direction of arrow 13 shown in FIG. 1 so as to function as a clamp valve for tubing 21 in guide groove 12.

One or more of the supports 9-11 may be configured to weld and/or cut tubes extending in grooves defined in the supports 9-11. For example, electric power to perform welding via supports 9-11 may be passed to the supports 9-11 via an electrical contact between the rotor 34 and a centrifuge stand. Various different components of the centrifuge may also be supplied with power via contact(s). In the embodiment of FIG. 1, the electric power is conveyed via electrical slip ring connectors 14, 15 between the rotor and stand portions of the centrifuge, wherein connector 14 is a rotating part of the centrifuge and connector 15 is a secured part in the centrifuge stand. As shown in FIG. 1, the centrifuge 34 may include a centrifuge motor 16 coupled to the rotor 1 so as to rotate the rotor 1 about the axis of rotation X. For example, the motor 16 may be coupled to the centrifuge rotor 1 by a driving belt 47 disposed in operative communication with a motor driving pulley 48 and a centrifuge driving pulley 49. A centrifuge rotation bearing 50 may cooperate with a rotating guide 51.

As shown schematically in FIG. 1, both the collection container 33 and filter 31 may be received in the center cavity 2. The filter 31 may be disposed in the cavity 2 in any number of different fashions. In one example, shown in FIG. 1, the filter 31 may be arranged in the cavity 2 so that components passing through the filter flow in a direction generally toward the axis of rotation X. In the embodiment of FIG. 1A, the filter 31 is oriented to position a filter inlet 31a above a filter outlet 31b. Due to centrifugal forces generated during rotation of the rotor 1, substances flowing through the filter 31 of FIG. 1A may flow in a horizontal direction (as viewed in FIG. 1A) as well as in the vertical direction.

As shown in FIG. 1A, the filter 31 is optionally disposed in a generally lateral orientation on a small ledge 32 extending into the cavity 2. A covering member such as inner lid 6 may be configured to contact and/or otherwise cover and hold filter 31 in place. For example, a projection 66 extending from the lid 6 and the ledge 32 may define a holder for the filter 31. Alternatively, the ledge 32 could be moved upwardly from the position shown in FIG. 1A and/or an inner part of the lid could extend slightly lower. In another alternative arrangement, the filter 31 may be positioned in the cavity 2 without being restrained, such as in the embodiment shown in FIG. 1.

FIG. 1B shows another embodiment including an alternative placement of filter 31. The filter 31 of FIG. 1B is positioned in a generally lateral orientation with the filter 31 being eccentric with respect to the axis of rotation X. In addition, the filter 31 of the embodiment of Fig. B is offset slightly from the rotational axis X so that the axis X does not intersect an interior of the filter 31. The filter 31 is positioned so that substances flowing through the filter 31 flow in a direction 95 generally facing toward the axis of rotation X.

FIG. 8 schematically shows an example of how the filter 31 of FIG. 1B may be configured. (In FIG. 8, the filter 31 and separation 4 are not drawn to scale.) As shown in that figure, the filter 31 has a filter inlet 31a and a filter outlet 31b at the respective ends of L-shaped tubing segments connected to a filter housing 31d defining an interior space containing a porous filtration medium 31c. The filter outlet 31b is located above the filter inlet 31a; and the filter inlet 31a is located closer than both the filter outlet 31b and filtration medium 31c to the axis of rotation X. The filter housing 31d defines a filter housing inflow port 31e and a filter housing outflow port 31f above the inflow port 31e. The filter housing outflow port 31f is closer than the filter housing inflow port 31e to the axis of rotation X. The filter housing outflow port 31f is also closer than the filtration medium 31c to the axis of rotation X.

In some examples, such as that of FIG. 8, the relative positioning of the filter inlet 31a, filter outlet 31b, housing inflow port 31e, housing outflow port 31f, and/or medium 31c, as well as the eccentric (and possibly also offset) positioning of the filter 31, may assist in clearing most (if not all) air from the interior of the filter, as compared to alternative filtering arrangements which might potentially cause air to be "locked" therein.

Figure 8A:
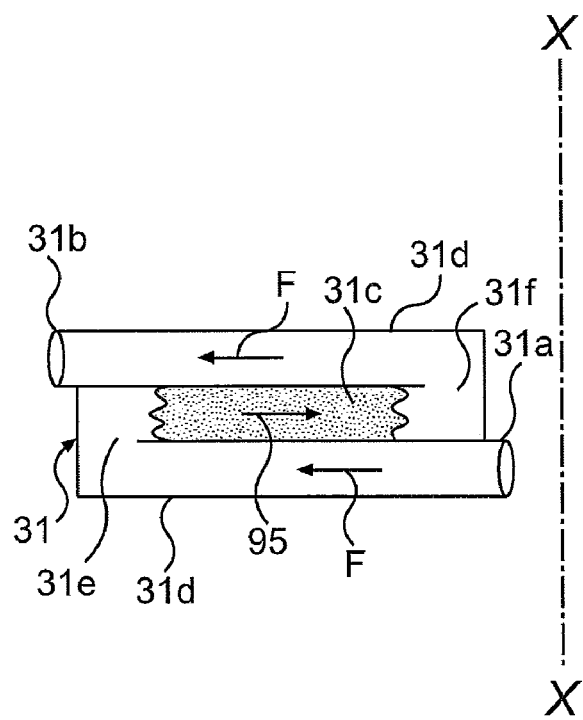
FIG. 8a is a schematic, partial cross-section view of an alternative filter configuration.

FIG. 8a shows another example of a filter 31 that could be used in the system. As shown in that figure, filter outlet 31b is located above filter inlet 31a; and filter inlet 31a is closer than both filter outlet 31b and filtration medium 31c to the axis of rotation X. In this example, rather than having the L-shaped tubing segments shown in FIG. 8, filter housing 31d defines flow passages leading to and from filter outlet 31b and filter inlet 31a, respectively, such that filter housing outflow port 31f is located closer than both filter housing inflow port 31e and medium 31c to the axis of rotation x. In addition, outflow port 31f is above inflow port 31e.

Figure 8B:
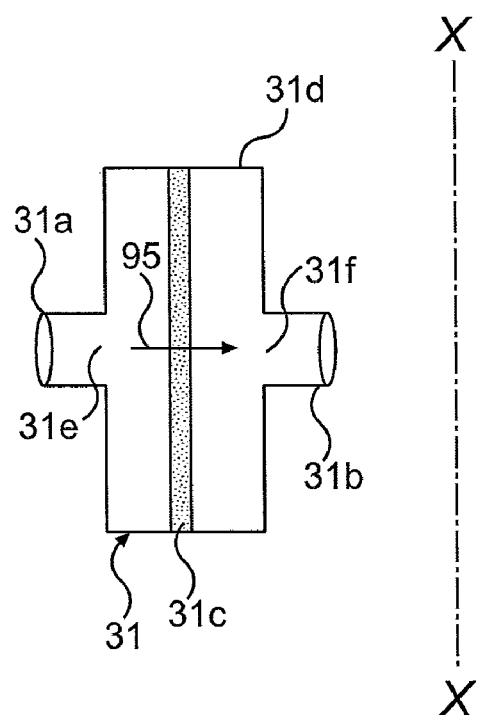
FIG. 8b is a schematic, partial cross-section view of another alternative filter configuration.

FIG. 8b shows a further example of a filter 31 that could be used in the system. For this example, housing inflow port 31e and housing outflow port 31f are at substantially the same relative positions as filter inlet 31a and filter outlet 31b, respectively. In contrast to the filter shown in FIG. 8a, filter housing outflow port 31f is closer than both filter housing inflow port 31e and filtration medium 31c to the axis of rotation X. In addition, the inlet 31a, inflow port 31e, outflow port 31f, and outlet 31b are at substantially the same level.

Further, filter outlet 31b is closer than both filter inlet 31a and filtration medium 31c to the axis of rotation X.

One feature in common with the filter examples of FIGS. 8, 8a, and 8b is that blood components flowing in an interior space containing filtration medium 31c flow in a direction 95 facing generally toward the axis of rotation X.

As partially shown in FIG. 1B, the filter 31 may be positioned at least partially in a slot 57 offset from the axis of rotation X. The slot 57 may be wholly or partially defined in lid 6. Alternatively, the slot 57 could be defined using a shelf and projection similar to those shown in FIG. 1A.

Although the embodiments of FIGS. 1, 1A, and 1B show the filter positioned beneath the top surface of the rotor 34, the filter 31 could alternatively be arranged partially or completely above the rotor's top surface. In some alternate embodiments, the filter may even be positioned at a location that is not within the centrifugal field generated by rotation of the rotor 1.

In the embodiments of FIGS. 1, 1A, and 1B, the portion of the centrifuge rotor defining the ring-shaped area 3 and the portion of the centrifuge rotor defining the center cavity 2 are positioned with respect to one another so that when the chamber 4 is received in the area 3 and the filter 31 is received in the cavity 2, the filter 31 is closer than the chamber interior 8 to the axis of rotation X, as schematically illustrated in FIG. 8. Such a positioning may avoid the filter 31 from being subjected to relatively high centrifugal forces while permitting substances being centrifugally separated in the chamber interior 8 to be subjected to such high forces. In some instances, it may be desired for such a reduced amount of centrifugal force to be applied to the filter 31. For example, in certain filter arrangements, exposure to relatively high centrifugal forces might cause certain potential problems associated with bursting of the filter housing, or perhaps negatively affect the filtration efficacy. For some filters, such as those that might not be significantly impacted by centrifugal forces, alternative positioning of the filter might be possible.

The filtration medium 31c shown in FIGS. 1A, 8, 8a, and 8b may be any form of porous medium, such as fibers combined together in a woven or unwoven form, loose fibers, foam, and/or one or more membranes, for example. The filtration medium 31c may be configured to filter leukocytes, platelets, and/or red blood cells.

The filter 31 could be configured in any known form. In some embodiments, the filter 31 may be a leukoreduction filter configured to filter leukocytes from blood components including a concentration of platelets. One example of such a filter is the LRP6 leukoreduction filter marketed by the Pall Corporation of Glen Cove, N.Y. Another example is the Sepacell PLS-10A leukocyte reduction filter marketed by Baxter Healthcare Corp. of Deerfield, Ill. A further example is the IMUGARD filter marketed by Terumo of Japan. It should be understood that other known leukoreduction filters could also be used and such filters optionally may be selected depending upon the process being undertaken.

As shown in FIG. 1B, the inner lid 6 includes one or more grooves 60 defined therein for receiving one or more tubing lines. A first tubing portion 21a places the blood component separation chamber (not shown in FIG. 1B) and filter 31 in flow communication with one another. Tubing 21 is flow coupled to the outlet of filter 31. The tubing 21 includes a second tubing portion 21b coupled to an outlet of the filter 31 and extending in a direction facing generally away from the rotation axis X. The tubing 21 also includes a third downstream portion 21c extending in a direction generally facing the axis of rotation X. The groove(s) 60 may be configured to receive at least some of the second and third tubing portions 21b and 21c.

In some embodiments, there may be lids (not shown) other than the lid 6 to account for a plurality of processes which may alternatively be performed by the system. As shown in FIG. 1B, the groove(s) 60 may be arranged to associate the tubing 21 with one or more other features of the embodiment. For example, the groove(s) 60 may be arranged to place the tubing 21 in cooperation/communication with the groove 12 of member 9 (and/or with an optical sensor 55 described below), among other things.

As shown in FIG. 2, the chamber 4 is optionally in the form of a bag defined by two sheets of a suitable plastic material (e.g., flexible and/or semi-rigid plastic material) joined together by circumferentially welding radially inner and outer edges 17 and 18. Between the welded edges 17 and 18, there is an open, ring-shaped chamber interior in which blood components are separated. The chamber 4 includes a central opening (e.g., aperture) 19 which primarily corresponds to the center cavity 2 opening. Such a structure may simplify access to the center cavity 2. The chamber 4 shown in FIG. 2 has respective guide holes 109, 110, and 111 for receiving supports 9-11, respectively, and thus positioning the chamber 4 with respect to the supports 9-11. The bag material surrounding the guide holes 109, 110, and 111 may be welded to strengthen the material around the holes. The guide holes 109, 110, and 111 optionally have an asymmetric arrangement (about rotational axis X) that is like that of the optional asymmetric orientation of the supports 9, 10, and 11 so as to facilitate orienting the chamber 4.

At least a portion of the chamber 4 may be formed of flexible and/or semi-rigid material so that the interior of the chamber 4 has a variable inner volume. For example, the chamber 4 may be formed of material permitting external pressure to be applied to the chamber so as to reduce the inner volume of the chamber 4. In some exemplary arrangements, the chamber 4 and possibly the other parts of the apparatus 100 may be formed of material comprising inert plastic.

The chamber 4 includes an inlet port 4a for passing blood components to the interior of the chamber 4 and an outlet port 4b for passing at least some centrifugally separated blood components from the chamber interior. Inflow tubing 20 and outflow tubing 21 are placed in flow communication with the ports 4a and 4b, respectively, on opposite facing sides of the chamber 4 via welded sleeve couplings 24. Each sleeve coupling 24 may be a securing part in the form of a short piece of tubing with a diagonally arranged flat securing collar which may be welded to the chamber 4, while permitting the respective tubing 20 and 21 to be welded to the coupling 24. Instead of being secured via such a sleeve coupling, the tubing could alternatively be secured to (and/or in) each respective welded edge, i.e. within welded edges 17 and 18.

Figure 6:
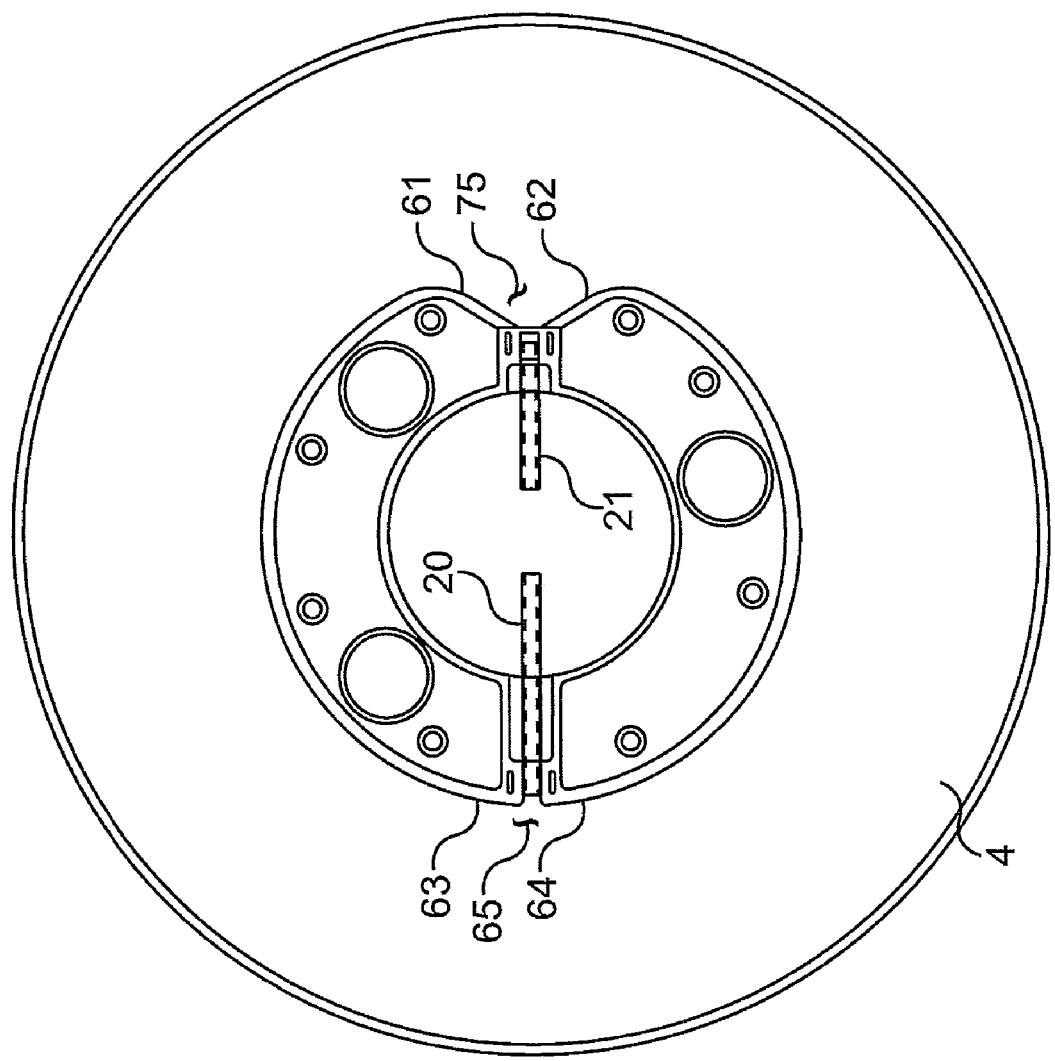
FIG. 6 is a top, partially schematic view of an alternative embodiment of a separation chamber.

An alternative embodiment of a chamber 4 is shown in FIG. 6, wherein, a sort of bay 75 is positioned at the outlet port leading to tube 21. This bay 75 is defined by a gradually tapered portion formed by weld portions 61 and 62 extending in a generally radial direction from the outlet port. (The chamber 4 shown in FIG. 2 may have a similar bay.) This type of arrangement may enable platelets to be received in a relatively non-abrupt or otherwise non-disruptive process. This may enhance the quality of the harvested platelets.

Referring again to FIG. 6, an inlet area 65 in the region of an inlet port leading from tube 20 does not have a tapered portion defined by weld portions 63, 64. This configuration may alleviate any potential capture of platelets (or some other desired product) so as to permit platelets to be available for harvesting at the outlet area 75.

When the chamber 4 is formed in a ring shape, as shown in the drawings, the chamber 4 and at least certain aspects of the centrifuge 34 may be configured like the separation chambers and associated centrifuges disclosed in one or more of the following patent documents: WO 87/06857, U.S. Pat. No. 5,114,396, U.S. Pat. No. 5,723,050, WO 97/30715, and WO 98/35757, for example. Many alternative arrangements are also possible.

Although the embodiments shown in the drawings include a separation chamber in the form of a ring-shaped bag, it should be understood that there are many alternative forms of separation chamber configurations that could be used. For example, the separation chamber could be in the form of a bag other than a ring-shaped bag. Alternatively, the separation chamber could be in other non-bag forms, such as, for example, in the form of one of the separation vessels disclosed in U.S. Pat. No. 6,334,842.

In one alternative embodiment (not shown), a filter similar to (or identical to) filter 31 could be positioned in tubing 20 to filter at least some blood components (e.g., leukocytes, platelets, and/or red blood cells) from substances being passing into the chamber 4.

Figure 3:
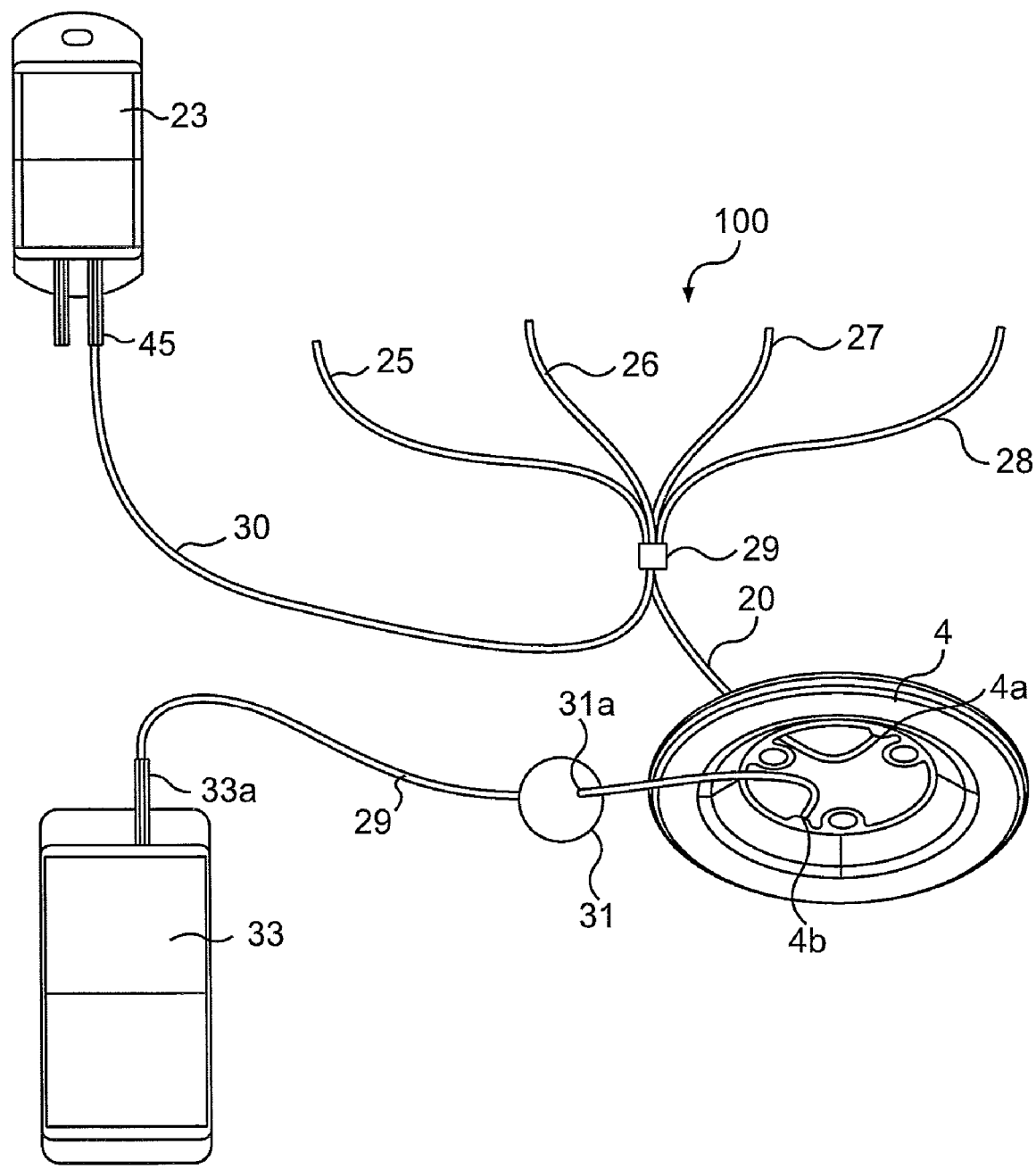
FIG. 3 is partially schematic view of an embodiment of an apparatus including the chamber and filter of FIG. 2.

FIG. 3 shows an embodiment of an apparatus 100 including the chamber 4 and filter 31 shown in FIG. 2. This exemplary apparatus 100 is in the form of a bag set for producing platelets from a buffy coat collection. The apparatus 100 further includes a bag 23 containing diluting solution, a solution tube 30, four connecting tubes 25-28 intended to be coupled (e.g., via welding) to respective bags containing previously prepared buffy coat products (not shown), and a multi-way connector 29 connecting the tubes 25-28 and 30 to the inflow tubing 20 coupled to the inlet port of chamber 4. From the chamber 4, the tubing 21 having filter 31 in-line is coupled to an inlet 33a of collection container 33, which is in the form of a bag. In an area where the solution tube 30 is coupled to the solution bag 23, there may be a blocking switch 45 (e.g., frangible member) capable of being placed in an open, flow-permitting position by bending the tube 30 and breaking open the connection so as to initiate the addition of diluting solution to bags (not shown in FIG. 3) connected to tubing lines 25-28. Before the blocking switch 45 is opened, solution tube 30 may be arranged in a guide groove 12 defined by one of the supports 9-11 so as to provide a clamp valve intended for controlling the addition of diluting fluid to buffy coat bags associated with lines 25-28

Although four connecting tubes 25-28 are shown in FIG. 3, any number of tubes may be used. For example, the number of connecting tubes may be between four and six or between four and eight.

The system embodiments of FIGS. 1, 1A, and 1B include a pump configured to pump at least some centrifugally separated blood components from the chamber 4 to the filter 31, and those embodiments also include a pressure sensor configured to sense pressure of the pumped blood components. As shown schematically in FIG. 9, a pump 80 may include a hydraulic fluid flow passage 88 passing through centrifuge rotor 1. One end of the hydraulic fluid flow passage 88 is in flow communication with a portion of ring-shaped area 3 positioned beneath the chamber 4 and separated from the chamber 4 via a flexible membrane 22. Another end of the hydraulic fluid flow passage 88 is in flow communication with a hydraulic fluid pressurizer 84 including a piston movable in a hydraulic fluid cylinder via a driver motor 82 (e.g., a stepper motor that moves a lead screw). Optionally, a hydraulic fluid reservoir 86 and associated hydraulic fluid valve 90 may be used to introduce and/or remove hydraulic fluid to/from the hydraulic fluid flow passage 88.

In response to a control signal from a controller 68, the driver motor 82 drives the piston of pressurizer 84 so as to pressurize or depressurize hydraulic fluid in the flow passage 88 (e.g., depending on the direction of travel of the pressurizer piston). The pressurization of the hydraulic fluid causes pressure to be applied to the chamber 4 via the hydraulic fluid pressing against membrane 22. The pressure applied to the chamber 4 causes the interior volume of the chamber 4 to become reduced and thereby pump centrifugally separated blood components from the chamber 4. Increasing the pressure of the hydraulic fluid causes an increase in the flow rate of the blood components pumped from the chamber 4. Conversely, a decrease of the hydraulic fluid pressure causes a decrease (or halting) of the pumped flow of blood components from the chamber 4.

Figure 9:
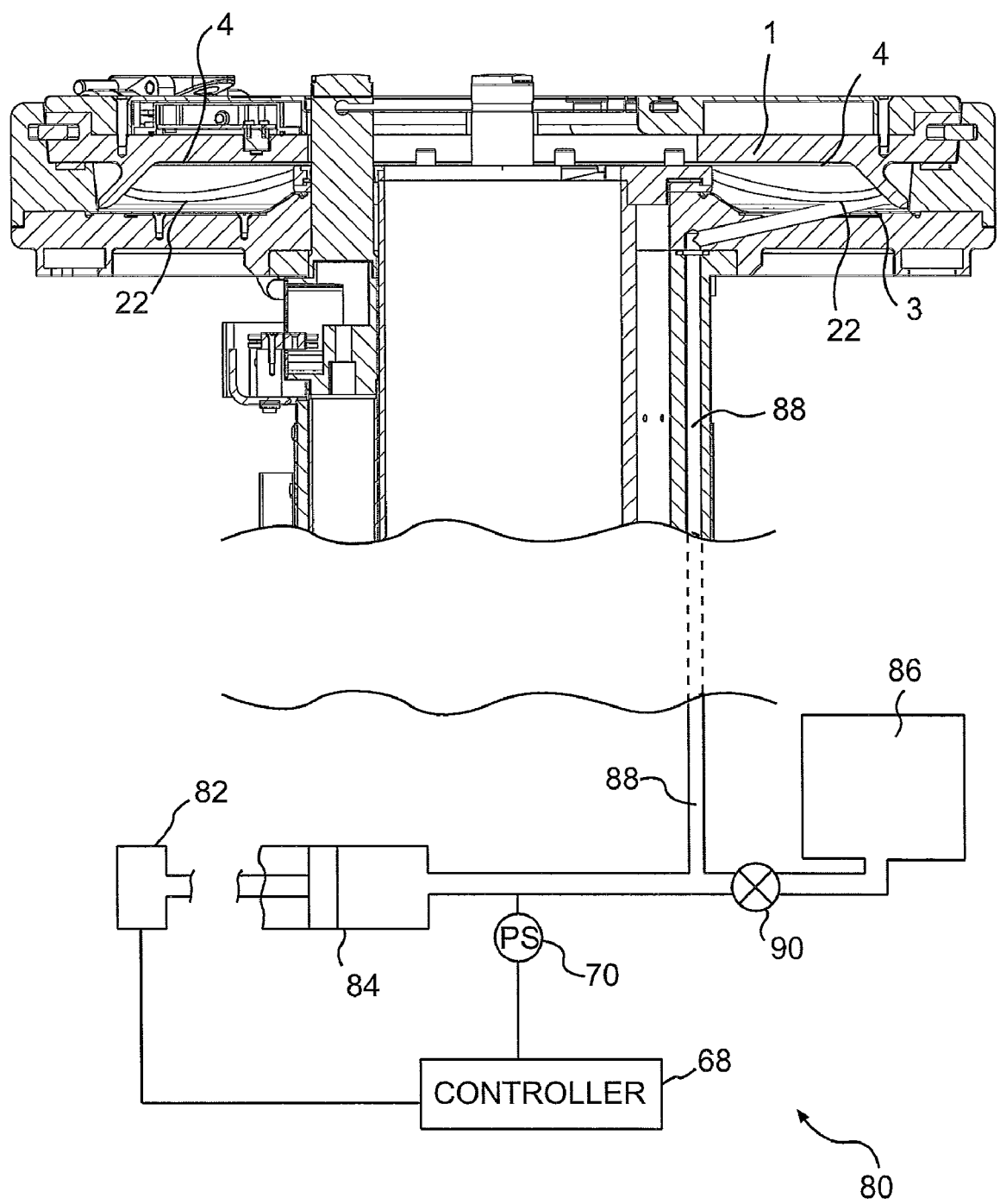
FIG. 9 is a schematic view of a hydraulically operated pump and pressure sensor associated with the system embodiments of FIGS. 1, 1A, and 1B.

The pressure of the hydraulic fluid is related to the pressure of blood components being pumped from the chamber 4. As shown in FIG. 9, a pressure sensor 70 is configured to monitor the pressure of the hydraulic fluid in the hydraulic fluid flow passage 88. Due to the relationship between the pressure of the hydraulic fluid and the pressure of the pumped blood components, the hydraulic fluid pressure sensed by the pressure sensor 70 reflects the pressure of the blood components pumped from the chamber 4. In other words, the pressure sensed by the pressure sensor 70 of FIG. 9 is essentially the same as (or at least proportional to) the pressure of the pumped blood components.

The hydraulic fluid may be any suitable substance. For example, the hydraulic fluid may be a fluid having a density slightly greater than that of packed red blood cells. One example of such a substance is Glycol. The hydraulic fluid may alternatively comprise oil.

A number of different pumping and/or blood component pressure sensing arrangements other than those shown in FIG. 9 are possible. For example, the amount of current needed to drive the driver motor 82 associated with the hydraulic fluid pressurizer 84 may indicate the pressure of both the hydraulic fluid and the blood components. In other examples, the pressure of the blood components could be sensed more directly (e.g., not via hydraulic fluid) using any type of pressure sensor.

The pump 80 may be controlled based at least partially on the pressure sensed by the pressure sensor 70. In the embodiment of FIG. 9, the controller 68 could be configured to control the driver motor 82 based at least partially on the pressure sensed by the pressure sensor 70. For example, the controller 68 could be configured such that the controller 68 calculates a difference between pressures sensed by the pressure sensor 70 in at least one time interval while blood components are pumped by the pump 80, determines when the calculated difference is at least a predetermined amount, and controls the pump 80 in response to at least the determination that the calculated difference is at least the predetermined amount. Such an arrangement could enable a feedback control of the pump 80, for example, when the pump is initially operated via a volume flow rate command.

As explained in more detail below, in a procedure attempting to collect a maximum number of platelets and a minimum number of white and red blood cells, the control of the pump 80 based at least partially on the sensed pressure may be used to stop the pumping of the blood components from the chamber 4 in response to an increased pressure reflecting that relatively viscous red blood cells are entering the filter 31 and causing an occlusion of flow through the filter 31.

The pressure sensed by the pressure sensor 70 could enable a determination of the location of one or more interfaces associated with separated blood components being pumped from the chamber 4. For example, the pressure sensed by the pressure sensor 70 could indicate the location of an interface between blood components and air present in the system at the startup of a blood component processing procedure. In such an example, an increase in pressure might reflect that an air-blood component interface is near (or at) a radially outward portion of a fluid flow path (e.g., in FIG. 1B, the location $F_0$). In another example, the pressure could provide an indication of the location of an interface between blood components having differing viscosities. For example, an increase of the pressure sensed by the pressure sensor 80 during the filtering of at least some blood components via the filter 31 could provide an indication that a blood component interface (e.g., between a first phase including primarily liquid (i.e., plasma and possibly one or more liquid additives) and platelets, and a second phase including primarily red blood cells and white blood cells) is located near (or at) the filter 31, and/or a particular location in the flow path leading to or from the filter 31, and/or a particular location in the chamber 4.

The pressure sensed by the pressure sensor 70 could reflect a "fingerprint" of the operation of the system. For example, the sensed pressure could reflect one or more of the following: a kinking of fluid flow lines; a leak (e.g., rupture) of the membrane 22, chamber 4, and/or flow path leading to and from the filter; an increased likelihood of platelet activation (e.g., a high pressure might reflect forcing of platelets through the filter 31); a defect and/or clogging associated with the filter 31; and/or a possible need for maintenance (e.g., an indication that the membrane 22 is worn).

The pressure sensed by the pressure sensor 70 could also be used to optimize (e.g., reduce) the time for processing (e.g., separation) of blood components. For example, when the pressure sensed by the pressure sensor 70 indicates a location of particular blood components, the pump 80 could be controlled to use differing flow rates for differing blood components (e.g., use a faster flow rate for pumping certain blood components, such as plasma).

In addition to pressure sensor 70, embodiments of the system may also include one or more optical sensors for optically sensing blood components, and the pumping of the blood components may also be controlled based on at least information sensed by the optical sensor(s). As shown schematically in FIGS. 1 and 1A, a first optical sensor 52 is positioned in the centrifuge rotor 1 adjacent the chamber 4 to optically sense blood components in the chamber 4. (Although not shown in FIG. 1B, the embodiment of FIG. 1B also includes such a sensor.) In addition, as shown in FIG. 1B, the system also may include a second optical sensor 55 positioned to optically sense blood components flowing through the tubing line 21 at the second tubing portion 21b, located downstream from the filter 31.

The optical sensors could be configured in the form of any type of optical sensor used in association with blood components. One example of an optical sensor may include a photocell. The first and second optical sensors 52 and 55 may be configured to detect a change of color of blood components. Such a change of color may be indicative of the location of an interface between differing blood component phases, such as an interface where one of the phases that defines the interface includes red blood cells.

The first optical sensor 52 may be located at a particular radial position on the centrifuge rotor 1 so as to sense when an interface has moved to that location in the chamber 4. For example, the pumping of blood components from the chamber 4 could be slowed 9 (e.g., via a reduction of hydraulic pressure with the arrangement of FIG. 9) in response to the first optical sensor 52 detecting an interface (e.g., an interface partially defined by red blood cells) approaching a radially inward location. Similarly, the second optical sensor 55 may detect the presence of an interface (e.g., an interface partially defined by red blood cells) along the flow path leading from the chamber 4. In some examples, the controller 68 could be configured so as to halt pumping of blood components from the chamber 4 in response to the second sensor 55 sensing an interface (e.g., an interface partially defined by red blood cells) and/or in response to a determination that the difference between pressures sensed by the pressure sensor 70 is at least a predetermined amount.

Figure 7:
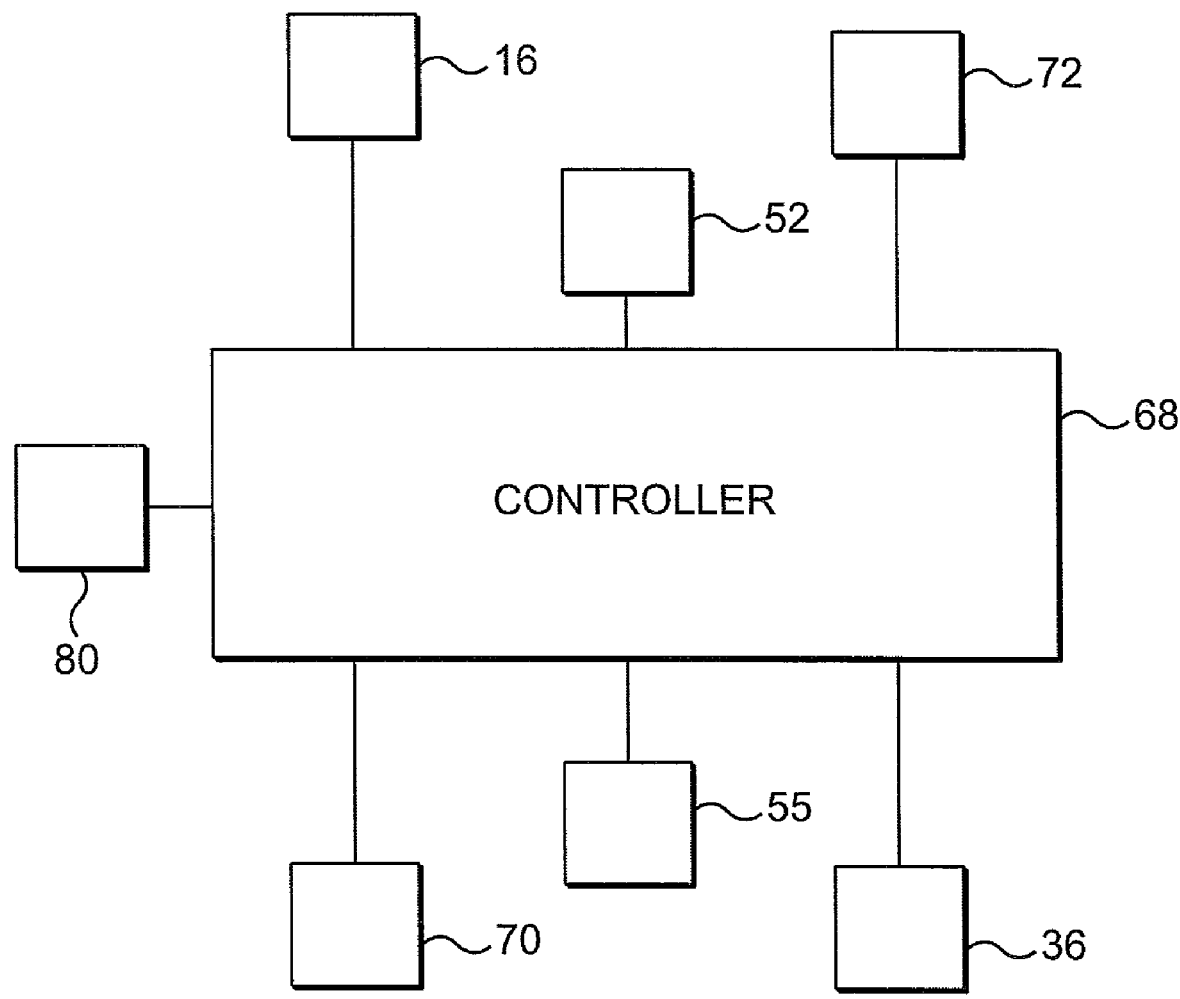
FIG. 7 is a schematic view of an example of a controller communicating with various possible system components.

FIG. 7 shows a schematic view of an example of the controller 68 that may be used to at least partially control certain features of the system. The controller 68 communicates with various system components. For example, the controller 68 could communicate with the pump 80, centrifuge motor 16, pressure sensor 70, first optical sensor 52, second optical sensor 55, valving structure 72 (e.g., the valves defined by supports 9, 10, 11), and a control panel 36. The controller 68 may be configured to cause rotation of the centrifuge rotor 1 during filtering of at least some blood components (e.g., leukocytes, platelets, and/or red blood cells) via the filter 31 received in the cavity 2. In some embodiments, this may enable centrifugal separation in the chamber 4 and filtering via the filter 31 to occur at least partially simultaneously in a somewhat on-line fashion, as compared to some other approaches where filtering takes place a period of time after initial centrifugal separation and removal of a separation chamber and possibly also a filter from a centrifuge rotor. Alternatively (or additionally), the controller 68 may be configured so that filtering via the filter 31 takes place at least some time after at least an initial separation of blood components in the chamber 4.

The controller 68 may control the rotational speed of the rotor 1. In addition, the controller 68 may control the pump 80 and/or valving structure 72 to control the pumping of substances flowing to and from the chamber 4 and the filter 31. The controller 68 may include a processor having programmed instructions provided by a ROM and/or RAM, as is commonly known in the art. Although a single controller 68 having multiple operations is schematically depicted in the embodiment shown in FIG. 7, the controlling may be accomplished by any number of individual controllers, each for performing a single function or a number of functions.

The controller 68 may be configured to pump hydraulic fluid at a specified flow rate. This flow rate may cause a blood component flow rate with a resultant pressure. The controller 68 may then take readings from the pressure sensor 70 and change the flow rate based on those reading so to control flow rate as a function of pressure measured.

A number of different pumping and/or blood component pressure sensing arrangements other than those shown in FIG. 9 are possible. In addition, there are a number of alternative ways in which the pumping of blood components from the chamber 4 could be controlled.

Figure 10:
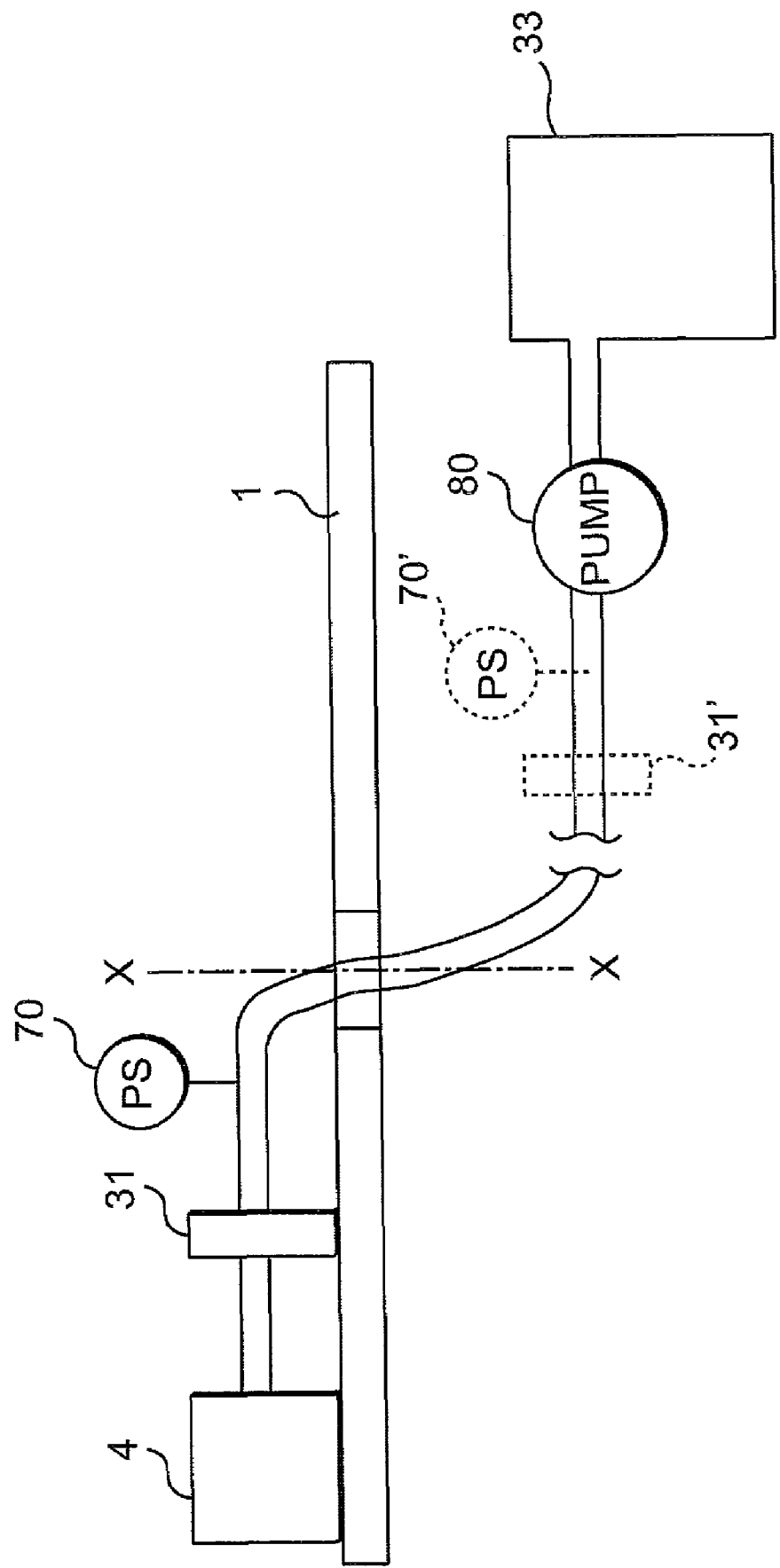
FIG. 10 is a schematic view of an alternative embodiment of a system associated with a centrifuge.

FIG. 10 schematically illustrates an embodiment where blood components are pumped from chamber 4 via a pump 80 positioned downstream from the filter 31 at a location outside of the centrifugal field generated by rotation of centrifuge rotor 1. Such a pump 80 could be configured in the form of a peristaltic pump or any other type of pump suitable for pumping blood components.

As shown schematically in FIG. 10, the pressure sensor 70 could directly sense the pressure of pumped blood components (rather than via hydraulic fluid) from a location on the centrifuge rotor 1. Alternatively (or additionally) the pressure of the blood components could be sensed directly by a pressure sensor 70' located outside of the centrifugal field caused by rotation of the rotor 1. Similarly, a filter 31' in place of (or in addition to) filter 31 could be located at a location outside of the centrifugal field of the rotor 1. Additionally, the collection container 33 may be located outside of the centrifugal field. In a further modification, the system might be modified so that there is no filter.

Figure 11:
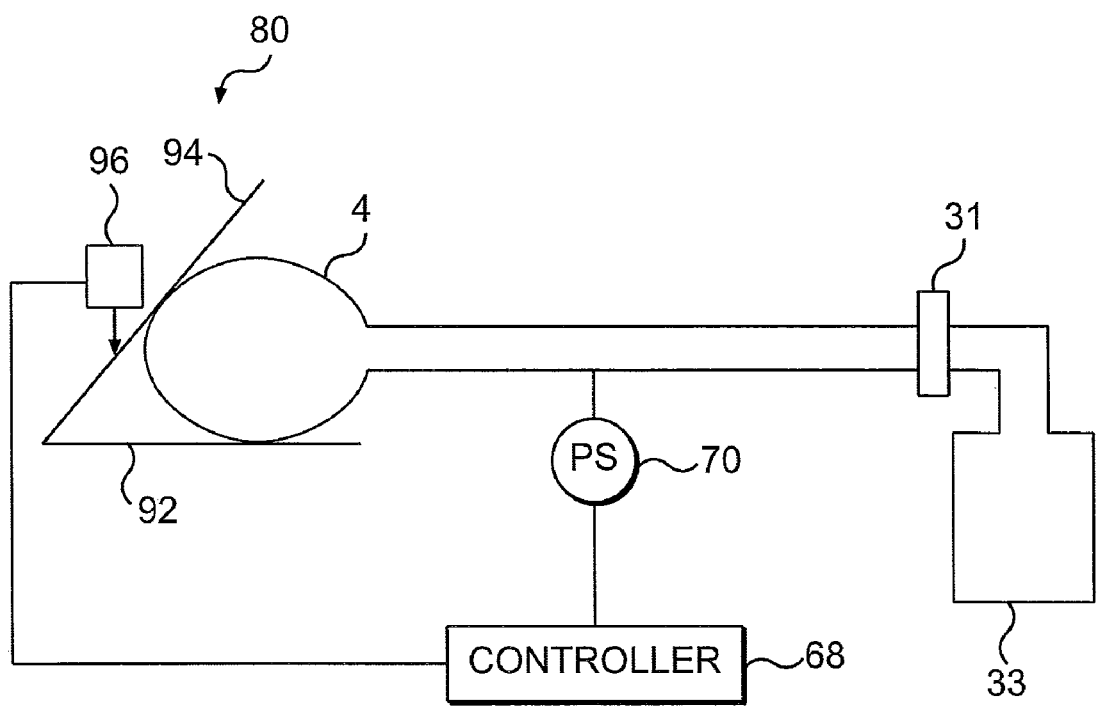
FIG. 11 is a schematic view of an alternative embodiment of a system associated with a blood component expresser.

In other embodiments, at least some structural features might not be part of a centrifuge structure. For example, FIG. 11 schematically shows an embodiment in the form a blood component expresser including a pump 80 configured to pump blood components from a chamber 4. The pump 80 of FIG. 11 includes a pair of clamping plates 92 and 94 that apply pressure to chamber 4 when a clamp driver 96 moves the clamping plates 92 and 94 together. A controller 68 controls the pump 80 based at least partially on pressure of pumped blood products sensed directly via the sensor 70. The chamber 4 could be a chamber that has been removed from a centrifuge rotor after blood components in the chamber 4 have been previously stratified in a centrifuging procedure.

Figure 12:
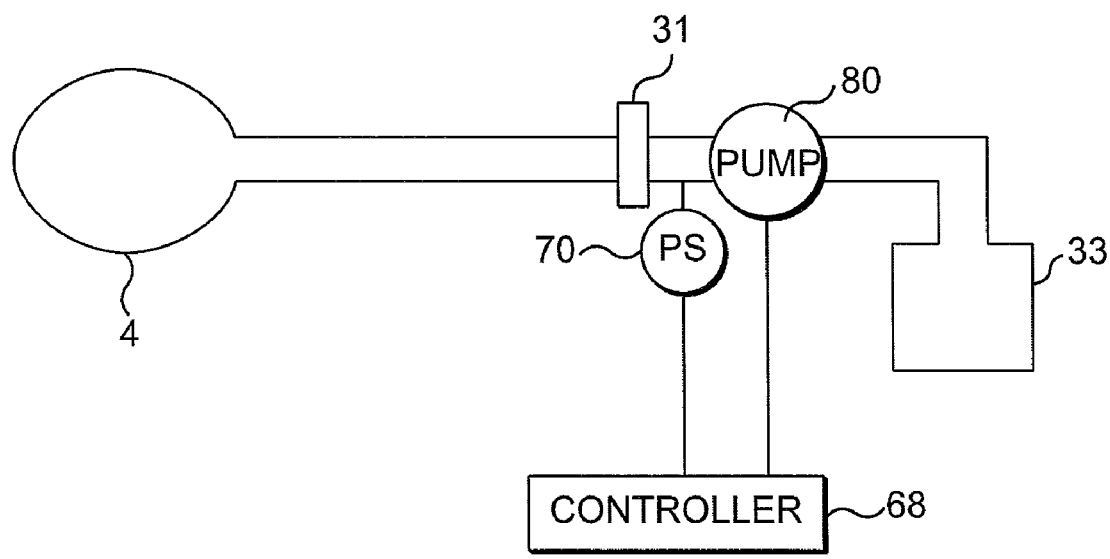
FIG. 12 is a schematic view of an alternative embodiment of a system associated with a blood component expressor.

FIG. 12 schematically shows an embodiment similar to that of FIG. 11, but substituting a pump 80 like that shown in FIG. 10.

The following provides a discussion of an exemplary blood processing method that could be practiced using the system embodiments shown in FIGS. 1, 1A, 1B, 2-4, and 6-9. Although the exemplary method is discussed in connection with the structure shown in those figures, it should be understood that the exemplary method could be practiced using alternative structure. (In addition, the structure shown in those figures could be used in alternative methods.)

FIG. 4 shows certain components of the apparatus shown in FIG. 3, but some of those components are drawn to a smaller scale or are not visible in FIG. 4. As shown in FIG. 4, centrifuge 34 is shown standing with its outer lid 35 completely open and locked in that position. The centrifuge inner lid 6 (see FIGS. 1 and 1A) has been omitted to show other parts more clearly. Also, the centrifuge rotor 1 and chamber 4 have, to a certain extent, been drawn in a simplified manner. The centrifuge control panel 36 is also shown schematically.

FIG. 4 illustrates four blood bags 37-40 containing buffy coat suspended in a cassette 41, which is mounted on the inside of the centrifuge outer lid 35. Buffy coat bags 37-40 have individual output lines connected by sterile welding to tube connectors 25-28 (see FIG. 3). The fluid content of the bags is introduced into the chamber 4 via the tubes 25-28 and connecting tube 20. After (or before) that, the buffy coat bags 37-40 may be supplied with washing fluid and/or diluting solution from diluting solution bag 23 suspended from a holder 44. The diluting solution contained in the bag 23 may be plasma or any other standard diluting solution. An example of a conventional diluting solution is a PAS (platelet additive solution), such as, e.g., T-Sol. Diluting solution bag 23 is suspended sufficiently high above bags 37-40 to allow the diluting solution to be added in sufficient amounts to these bags as soon as blocking switch 45 in tube 30 and a clamp valve in support 11, through which tube 30 is passed, are opened. Communication between bags 37-40 and chamber 4 proceeds via tube 20 which in turn passes through a clamp valve in support 10, for example, for controlling fluid communication. After the addition of diluting solution in sufficient amounts to bags 37-40, a motor (not shown) connected with the cassette 41 may be started and operated to move the cassette 41 back and forth in a curved pendulum movement 42 (or alternatively a complete (or substantially complete) rotational movement) until all the concentrate substance in the buffy coat bags 37-40 is resuspended.

Various arrangements may cause the agitation movement of the cassette 41. For example, the motor driving the cassette movement may be associated with a gear box, or there may be a crank function or control of the motor. It may also be theoretically possible to use a hydraulic motor, but it might have a slower shaking speed and longer mixing time.

Then, the built-in clamp valve in the support member 10 may be opened so as to cause flow of substantially all of the substance from the bags 37-40 to the chamber 4 via the tubing 20. The tube 20 in support 10 may then be sealed by sterile welding provided by the support 10 so as to block fluid communication through the tube 20, and thereafter (or substantially simultaneously therewith) the support 10 may cut the tube 20, so that the empty bags 37-40 and bag 23 with any possible solution and/or concentrates from the buffy coat diluting solution mixture may be disposed. If desired, the flushing out of the buffy coat bags 37-40 could be carried out in one, two, or several consecutive flushing operations. After flushing out the buffy coat bags, cassette 41 and holder 44 may then be removed from the centrifuge lid 35 and thereafter the centrifuge lid 35 may then be closed and a centrifuging operation may be carried out.

Before centrifuging, the chamber 4 is placed in the ring-shaped area 3 (see FIGS. 1 and 1A) and the collection container 33 (see FIGS. 1, 1A and 3) and filter 31 are placed in the center cavity 2 (see FIGS. 1, 1A, and 1B). During centrifuging, the centrifuge rotor 1 is rotated about the axis of rotation X, thereby causing the blood platelet product to be separated from the other buffy coat components (e.g., red and white blood cells) in the chamber 4. Then, after (or in some embodiments, during) that separation, at least some of the platelet product may be pumped to the collection container 33 by increasing the pressure of hydraulic fluid passed into the ring-shaped area 3 under the membrane 22 shown in FIG. 9, and thereby applying external pressure to the chamber 4 that causes a reduction of the volume of an interior of the chamber 4. As is understood in the art, such a pressure applied by hydraulic fluid may occur during continued centrifugation (continued rotor spinning). It otherwise may be applied before rotor rotation has begun or even after rotation has halted.

The pumped blood components are removed from the chamber 4, optionally filtered by the filter 31, and then conveyed to collection container 33. As shown in FIG. 1B, arrows F show flow through portions of the filter 31 and the tubing line 21 (which passes through the second sensor 55 and support member 9) and thence into collection container 33. The flow path of material out of chamber 4 begins through first tubing portion 21a upstream from filter 31. Flow through tubing portion 21a emanates first from chamber 4, then travels through or near the axis of rotation X where the centrifugal forces are the lowest (zero or very near thereto) of any point in the system. The application of hydraulic pressure (and/or the centrifugal force) continues to then push the flow into the filter 31. As shown in FIGS. 1B and 8, the blood components may flow in an interior space of the filter housing 31d in a direction 95 facing generally toward the axis of rotation X. After exiting the filter housing, the blood components flow in a direction generally facing away from the axis of rotation X, through the second tubing line portion 21b, radially outwardly and through the second optical sensor 55. Then, the flow reaches its radially outermost point of travel, here indicated as point $F_0$, relative to the axis of rotation X. Flow then proceeds roughly inward via third tubing portion 21c, while passing through the support member 9, and the valving and/or sealing mechanism therein. The flow then proceeds to the container 33 disposed in the central cavity 2.

The filter 31 (e.g., a leukoreduction filter) may be configured to filter at least some undesired components. For example, where the desired product is platelets, the filter 31 may filter leukocytes and/or red blood cells. The filtration may occur substantially simultaneously with the removal (e.g., pumping) of components from the chamber 4, and also may be performed at least partially during rotation of the centrifuge rotor 1.

The exemplary method further includes optical sensing of blood components via the first and second optical sensors 52 and 55. In the exemplary method, the flow rate at which blood components are pumped from the chamber 4 may be reduced when the first optical sensor 52 senses that an interface (e.g., an interface between desired lighter substance (e.g., platelets) and a darker non-desired concentrate product (e.g., red blood cells and/or leukocytes)) is approaching a radially inward location (e.g., a location at or near the tubing 21). For example, such a reduction of the flow rate might be achieved by reducing the hydraulic pressure applied to the membrane 22 shown in FIG. 9.

The pumping of blood components from the chamber 4 may be interrupted or halted when the second optical sensor 55 senses an interface (e.g., an interface defined at least partially by red blood cells).

The exemplary method also includes sensing the pressure of blood components pumped from the chamber 4. In the embodiment shown in FIG. 9, the pressure of the pumped blood components is sensed via sensing of the pressure of the hydraulic fluid used to pump the blood components from the chamber 4.

Figure 5:
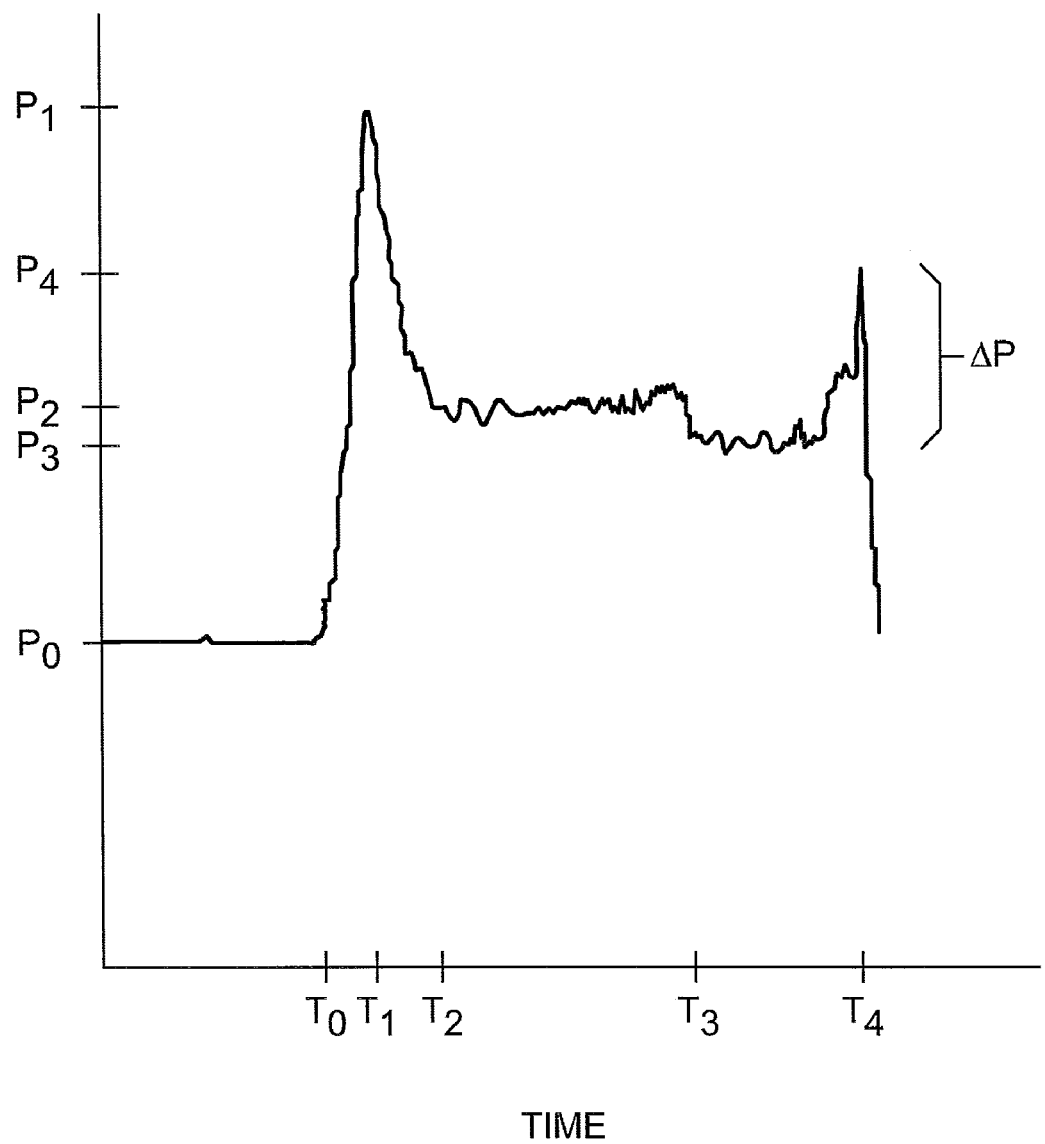
FIG. 5 is a graph showing pressure plotted over time in connection with an example involving the embodiment of FIG. 1B.

FIG. 5 illustrates an exemplary graph showing pressure sensed by the pressure sensor 70 of FIG. 9 relative to time during the processing of blood components in the exemplary method. Prior to a time $T_0$, there is relatively little (or no) sensed pressure because there is some initial time that may be dedicated to mere centrifugation/rotation of the centrifuge rotor 1 to effect the separation of the blood components into stratified layers before much hydraulic pressure is added to pump the blood products (in some alternative examples, pressure may be added sooner (or later) and perhaps even from the beginning of the rotation). At time $T_0$, the pressure of the hydraulic fluid is increased to begin pumping of blood components from the chamber 4. In some examples, the controller 68 could provide a relatively constant volume flow rate of hydraulic fluid, and, as described below, the hydraulic fluid flow could be altered based on sensed pressure feedback.

The initial pumping of blood components from the chamber 4 pushes an interface defined by the blood components and air initially present in the system at the beginning of the centrifugation. An increased amount of hydraulic pressure (and corresponding increase in pressure of the pumped blood components) occurs up until there is a peak of pressure $P_1$ at a time $T_1$. The pressure peak at time $T_1$ provides an indication that the air-blood component interface (e.g., interface between air and platelet rich plasma) has reached a particular location in the flow path defined by the system. For example, the pressure peak at time $T_1$ may represent that the air-blood component interface is located in the filter 31. Alternatively, the pressure peak at time $T_1$ may represent a form of "siphon" effect associated with pumping the air-blood component interface to the radially outermost flow path point $F_0$ shown in FIG. 1B. After reaching the point $F_0$, substances may encounter a bit of resistance due to centrifugal forces (which also contribute to keeping heavier phase materials at further radii from the axis of rotation) encountered when flowing back inwardly toward a lesser radius (which describes all points in the flow other than point $F_0$). Thus, a sort of back pressure may be built up.

After the air-blood component interface has been pumped past the location identified by the pressure peak at time $T_1$, the pressure reaches a reduced pressure level $P_2$ at time $T_2$. In a time period from $T_2$ to $T_3$, the pressure remains substantially constant at level $P_2$ while blood components (e.g., plasma, possible additive solution(s), and platelets) are pumped from the chamber 4, through the filter 31, and into the collection container 33. In the example represented by the graph of FIG. 5, the controller 68 has reduced the hydraulic pressure level to $P_3$ at time $T_3$ in response to the first optical sensor 52 sensing an interface defined at least partially by red blood cells in the chamber 4. The reduction of the hydraulic pressure causes a corresponding reduction of the pressure of the pumped blood components as well as a reduction of the flow rate of the pumped blood components (as compared to that in the time interval from $T_2$ to $T_3$). The reduction of the flow rate of the pumped blood components may reduce the likelihood that a substantial number of red and white blood cells will pass into the collection container 33. Additional flow rate reductions may also be possible for alternative examples.

The sensed pressure remains relatively constant at pressure $P_3$ immediately after time T3 and then the sensed pressure increases somewhat rapidly. The increased pressure represents that an interface defined between a phase of relatively low viscosity blood components (e.g., primarily liquid (i.e., plasma and possible liquid additive(s)) and platelets) and a phase of relatively high viscosity blood components (e.g., primarily red blood cells and white blood cells) is beginning to enter the filter 31. The relatively high viscosity blood cells (e.g., red blood cells) are unable to pass through the filter 31 as easily as liquids and other relatively low-viscosity components. As the relatively viscous blood components continue to enter the filter 31, they become "packed" in the filter 31 and cause an increasing back pressure sensed by the pressure sensor 70.

The controller 68 receives signals indicative of the pressure sensed by the pressure sensor 70. In the exemplary time interval from $T_3$ to $T_4$, the controller 70 calculates the difference between maximum and minimum pressures sensed by the pressure sensor 70, and the controller 70 determines when that calculated difference exceeds a predetermined amount. Then, in response to such a determination, the controller 70 controls the system so as to cause a significant reduction of hydraulic pressure and corresponding halting or ending of the pumping of blood components from the chamber 4 (e.g., the piston of pressurizer 84 could be retracted and/or valve 90 shown in FIG. 9 could be opened).

In the example shown in FIG. 5, at time $T_4$, the pressure reaches a peak at $P_4$ sufficient to cause a pressure difference $\Delta P$ (the difference between $P_4$ and $P_3$) indicating that the location of the interface defined by the viscous blood components has been pumped to (and possibly slightly beyond) the filter 31. In response to that pressure difference $\Delta P$ being determined by the controller 68, the controller 68 discontinues the pumping of blood components from the chamber 4 so that an excessive number of the viscous blood components will not be passed to the collection container 33. Accordingly, the pressure after $T_4$ reflects that hydraulic pressure is no longer applied to the chamber 4.

In some alternative examples, the system may be configured so that in response to a sufficient pressure difference, the pressure of the hydraulic flow may be altered (increased or decreased) to continue pumping of blood components at a different flow rate. This could happen multiple times during a single processing procedure.

For the example shown in FIG. 5, the pressure difference $\Delta P$ may be about 0.2 bar. Many other differentials could be used depending on a number of factors.

The generally flat portions of the pressure diagram (e.g., between $T_2$ and $T_3$ or between $T_3$ and $T_4$) indicate that there are no significant discrete phases of blood components passing from the chamber 4. Those flat portions might be interpreted as an indication of a desired flow rate. Such a flow rate may be determined in advance of a blood processing procedure and used as a form of feedback control so that when the desired flow rate is reached (as measurable by a discrete sensor (not shown)), the pressure may be leveled as shown and maintained, before encountering a pressure difference indicating a possible condition where it might be desire to cease (or otherwise alter) hydraulic pressure.

In some instances, the actual level of relatively steady pressure sensing (e.g., e.g., between $T_2$ and $T_3$ or between $T_3$ and $T_4$) might not be the same or even nearly the same value from one run to another. Thus, the interpretation of the pressure difference may not be determined by any particular pressure point, but rather may be expressed as and/or be dependent upon a certain minimum change in pressure regardless of the starting or ending pressure level.

The sensing of the pressure to determine the location of interfaces between phases could be used even in some blood component processing procedures that do not include centrifugation separation and/or filtration. For example, in a procedure that includes centrifugation, but not filtration, the sensing of pressure might be used to determine when an interface reaches a radially outermost position (similar to the position $F_0$ shown in FIG. 1B).

After an identification of the location of a blood component interface via the pressure sensing and/or the optical sensing (e.g., whichever detects the interface first), there could be a time delay before the pumping of blood components from the chamber 4 is discontinued. For example, in a procedure where platelets are being collected, at least a slight time delay might maximize a platelet collection while presenting a relatively low risk of causing a significant number of red and white blood cells to be collected along with the platelets.

When the pumping of blood components has been discontinued, the tubing 21 may be clamped shut (via the optional clamp associated with one or more of supports 9-11) and possibly also sealed and cut via sterile welding supplied by one or more of the supports 9-11 (e.g., support 9). Thereafter, the chamber 4 containing non-desired concentrates of particular blood components (e.g., red blood cells, etc.), may be removed from the centrifuge and disposed.

Figure 13:
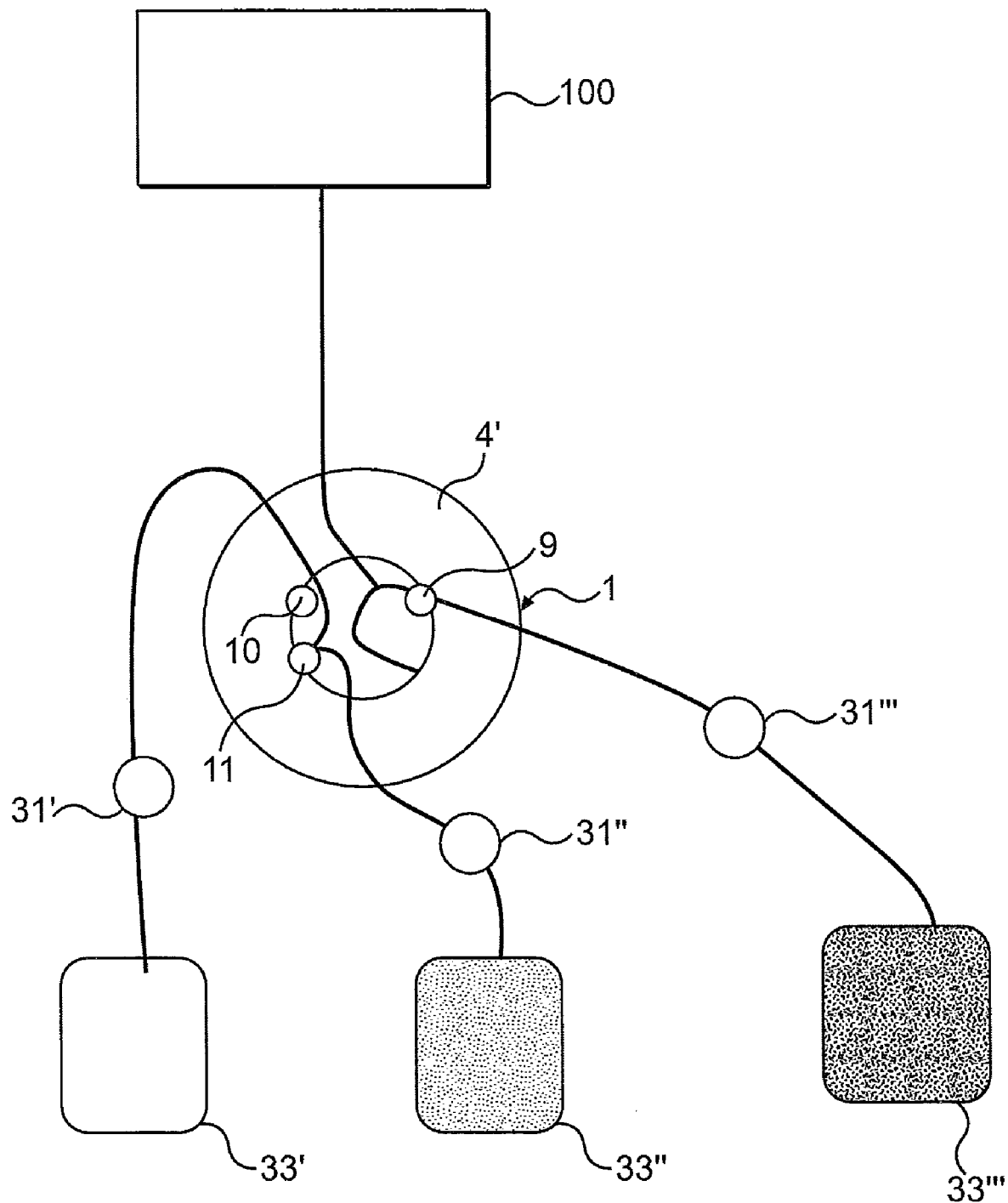
FIG. 13 is a schematic view of an embodiment of a system configured to process whole blood.

Systems and methods in accordance with the invention may be used in the processing of whole blood. For example, FIG. 13 schematically illustrates an embodiment of a system configured to process whole blood. As shown in that figure, whole blood from a whole blood source 100 (e.g., one/or more donors, and/or one or more containers containing blood donated by one or more donors) may be introduced into a chamber 4', which may be configured at least similar to the chamber 4 discussed above. For example, the chamber 4' may include a variable volume interior that may be reduced via hydraulic pressure so as to pump centrifugally separated blood components from the chamber 4'. As discussed in some of the above examples, alternative pumps may also be used. The pumping may optionally be controlled based on pressure sensing and/or optical sensing in a manner at least similar to that discussed above in connection with FIGS. 1, 1A, 1B, 5, 7, and 9-12.

The chamber 4' may include a single outlet or more than one outlet. In the example shown in FIG. 13, separate outlets may be associated with removal of particular blood components from the chamber 4'. In addition, a plurality of collection containers 33', 33", and 33'" may be respectively flow coupled to those outlets so as to collect separate blood components separated in the chamber 4'. For example, the collection container 33' may be used to collect a platelet product, collection container 33" may be used to collect a plasma product, and collection container 33'" may be used to collect a red blood cell product. One or more of the containers 33', 33", and 33'" may be either received in centrifuge rotor 1 or positioned at a location outside of the centrifugal field.

One or more of filters 31', 31", and 31'" may be associated with each of the respective flow paths leading from the chamber 4' to the containers 33', 33", and 33'". The filters 31', 31", and 31'" may be configured at least similar to filter 31 discussed above. One or more of the filters 31', 31". and 31'" may either be received in a portion of the centrifuge rotor 1 or located outside of the centrifugal field. Although FIG. 13 shows a separate, respective filter 31', 31", 31'" associated with each of the flow paths leading from the chamber 4', many other arrangements are possible. For example, one or more of the filters 31', 31", and/or 31'" (e.g., filter 31") may be omitted, and/or the filter outlets may be coupled to more than one collection container, and/or a single filter may be used for multiple flow paths.

In the embodiment of FIG. 13, one or more controllable clamps associated with one or more the supports 9, 10, 11 may be used to control flow of substances to and/or from the chamber 4'. One or more welders associated with one or more of the supports 9, 10, and 11 may be used to seal tubing lines leading to the containers 33', 33", and 33'". For example, such clamps and welders may be operated during rotation of the rotor 1.

In some alternative embodiments, other optional components, accessories and/or methods may be used in addition or in lieu of certain features described hereinabove. An example is a leukoreduction system, involving an LRS® chamber described in numerous publications including various U.S. and foreign patents (e.g., U.S. Pat. No. 5,674,173, among others). Other potential accessory devices may include sampling devices of numerous types including, for example, bacteria screening devices referred to as Bact-T Alert® devices.

In addition, an adapted database associated with a barcode reader may be utilized to make all the blood products processed by the system directly traceable and that database may also contain all control criteria for feasible blood product processing stages of the system.

It will be apparent to those skilled in the art that various modifications and variations can be made to the structure and methodology described herein. Thus, it should be understood that the invention is not limited to the subject matter discussed in the specification. Rather, the present invention is intended to cover modifications and variations.

What is claimed is:

1. A method of processing blood components, comprising:
   rotating a chamber about an axis of rotation,
   wherein blood components are centrifugally separated in the interior of the chamber
   pumping at least some of the centrifugally separated blood components from the chamber;
   filtering the pumped blood components with a filter so as to filter at least some of at least one blood component from the pumped blood components, wherein the filter comprises a porous filtration membrane;
   sensing pressure of the blood components pumped to the filter; and
   controlling the pumping based on at least the sensed pressure.

2. The method of claim 1 wherein the pumping occurs during rotation of the chamber.

3. The method of claim 1 wherein a centrifuge is used to rotate the chamber, and wherein said at least some separated blood components are pumped from the chamber while the chamber is received on a rotor of the centrifuge.

4. The method of claim 3, further comprising causing at least one valving member on the centrifuge rotor to control flow of at least some of the blood components during rotation of the rotor.

5. The method of claim 4, wherein the valving member comprises a tubing clamp.

6. The method of claim 3, further comprising causing at least one sealing member on the centrifuge rotor to create a seal during rotation of the rotor.

7. The method of claim 6, wherein the sealing member comprises a tubing welder.

8. The method of claim 1 wherein a centrifuge is used to rotate the chamber, and wherein said at least some separated blood components are pumped from the chamber after the chamber is removed from a rotor of the centrifuge.

9. The method of claim 1, further comprising rotating the filter about an axis of rotation during the filtering.

10. The method of claim 9, wherein the filter comprises a filter housing defining an interior space containing the porous filtration medium, and wherein the method comprises flowing blood components in the interior space in a direction facing generally toward the axis of rotation.

11. The method of claim 1, wherein the chamber is configured so that an interior of the chamber has a variable volume, and wherein the pumping comprises reducing the volume of the interior of the chamber.

12. The method of claim 11, further comprising applying pressure to the chamber via hydraulic fluid.

13. The method of claim 1, further comprising
   calculating a difference between pressures sensed in at least one time interval,
   determining when the calculated difference is at least a predetermined amount, and
   controlling the pumping in response to at least the determination that the calculated difference is at least the predetermined amount.

14. The method of claim 1, further comprising optically sensing the pumped blood products, and controlling the pumping based on at least one of optically sensed information and sensed pressure.

15. The method of claim 14, wherein optically sensing comprises optically sensing blood components in the chamber.

16. The method of claim 14, wherein optically sensing comprises optically sensing blood components in a tubing line in flow communication with the filter.

17. The method of claim 14, wherein optically sensing comprises optically sensing blood components in the chamber and optically sensing blood components in a tubing line in flow communication with the filter.

18. The method of claim 1, wherein the method further comprises passing the filtered blood components into at least one collection container.

19. The method of claim 1, wherein the blood components in the chamber are blood components of a buffy coat.

20. The method of claim 1, wherein whole blood is processed in the method.

21. A method of processing blood components, comprising:
rotating a chamber about an axis of rotation, wherein blood components are centrifugally separated in the chamber;
pumping at least some of the centrifugally separated blood components from the chamber;
sensing pressure of pumped blood components;
calculating a difference between pressures sensed in at least one time interval;
determining when the calculated difference is at least a predetermined amount; and
controlling the pumping in response to at least the determination that the calculated difference is at least the predetermined amount.

22. The method of claim 21, wherein the pumping occurs during rotation of the chamber.

23. The method of claim 21, wherein the chamber is rotated via a centrifuge rotor, and wherein the method further comprises causing at least one valving member on the centrifuge rotor to control flow of at least some of the blood components during rotation of the rotor.

24. The method of claim 23, wherein the valving member comprises a tubing clamp.

25. The method of claim 21, wherein the chamber is rotated via a centrifuge rotor, and wherein the method further comprises causing at least one sealing member on the centrifuge rotor to create a seal during rotation of the rotor.

26. The method of claim 25, wherein the sealing member comprises a tubing welder.

27. The method of claim 21, further comprising filtering the pumped blood components with a filter so as to filter at least some of at least one blood component from the pumped blood components, wherein the filter comprises a porous filtration membrane.

28. The method of claim 27, wherein the rotating further comprises rotating the filter about the axis of rotation.

29. The method of claim 28, wherein the filter comprises a filter housing defining an interior space containing the porous filtration medium, and wherein the method comprises flowing blood components in the interior space in a direction facing generally toward the axis of rotation.

30. The method of claim 21, wherein the chamber is configured so that an interior of the chamber has a variable volume, and wherein the pumping comprises reducing the volume of the interior of the chamber.

31. The method of claim 30, further comprising applying pressure to the chamber via hydraulic fluid.

32. The method of claim 21, further comprising optically sensing the pumped blood products, and controlling the pump based on at least one of optically sensed information and sensed pressure.

33. The method of claim 32, wherein optically sensing comprises optically sensing blood components in the chamber.

34. The method of claim 32, wherein optically sensing comprises optically sensing blood components in a tubing line in flow communication with the filter.

35. The method of claim 32, wherein optically sensing comprises optically sensing blood components in the chamber and optically sensing blood components in a tubing line.

36. The method of claim 21, wherein the method further comprises passing at least some of the pumped blood components into at least one collection container.

37. The method of claim 21, wherein the blood components in the chamber are blood components of a buffy coat.

38. The method of claim 21, wherein whole blood is processed in the method.

39. A method of determining a location of at least one interface during processing of blood components, comprising:
pumping at least some centrifugally separated blood components from a chamber;
sensing pressure of the pumped blood components; and
determining a location of at least one interface based on the sensed pressure, wherein the interface is associated with the pumped blood components.

40. The method of claim 39, wherein the interface comprises at least one of an interface between blood components and air, and an interface between differing blood components.

41. The method of claim 39, further comprising rotating a chamber about an axis of rotation, wherein blood components are centrifugally separated in the chamber.

42. The method of claim 41, wherein the pumping occurs during rotation of the chamber.

43. The method of claim 41, wherein the chamber is rotated via a centrifuge rotor, and wherein the method further comprises causing at least one valving member on the centrifuge rotor to control flow of at least some of the blood components during rotation of the rotor.

44. The method of claim 43, wherein the valving member comprises a tubing clamp.

45. The method of claim 41, wherein the chamber is rotated via a centrifuge rotor, and wherein the method further comprises causing at least one sealing member on the centrifuge rotor to create a seal during rotation of the rotor.

46. The method of claim 45, wherein the sealing member comprises a tubing welder.

47. The method of claim 41, further comprising filtering pumped blood components with a filter so as to filter at least some of at least one blood component from the pumped blood components, wherein the filter comprises a porous filtration membrane.

48. The method of claim 47, wherein the rotating further comprises rotating the filter about the axis of rotation.

49. The method of claim 48, wherein the filter comprises a filter housing defining an interior space containing the porous filtration medium, and wherein the method comprises flowing blood components in the interior space in a direction facing generally toward the axis of rotation.

50. The method of claim 39, further comprising filtering pumped blood components with a filter so as to filter at least some of at least one blood component from the pumped blood components, wherein the filter comprises a porous filtration membrane.

51. The method of claim 39, wherein the chamber is configured so that an interior of the chamber has a variable volume, and wherein the pumping comprises reducing the volume of the interior of the chamber.

52. The method of claim 51, further comprising applying pressure to the chamber via hydraulic fluid.

53. The method of claim 39, further comprising optically sensing the pumped blood products, and wherein the location of the location of the at least one interface is based on the sensed pressure and optically sensed information.

54. The method of claim 39, wherein the blood components in the chamber are blood components of a buffy coat.

55. The method of claim 39, wherein whole blood is processed in the method.

* * * * *